(12) United States Patent
Glass et al.

(10) Patent No.: US 10,330,673 B2
(45) Date of Patent: Jun. 25, 2019

(54) FLUORESCENT CHEMICAL SENSOR FOR BIOLOGICAL AMINES

(71) Applicant: The Curators of the University of Missouri, Columbia, MO (US)

(72) Inventors: Timothy Glass, Columbia, MO (US); Kevin Gillis, Columbia, MO (US); Kenneth Hettie, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 398 days.

(21) Appl. No.: 14/778,225

(22) PCT Filed: Mar. 21, 2014

(86) PCT No.: PCT/US2014/031490
§ 371 (c)(1),
(2) Date: Sep. 18, 2015

(87) PCT Pub. No.: WO2014/153533
PCT Pub. Date: Sep. 25, 2014

(65) Prior Publication Data
US 2016/0274091 A1    Sep. 22, 2016

Related U.S. Application Data

(60) Provisional application No. 61/852,851, filed on Mar. 21, 2013.

(51) Int. Cl.
| C07D 403/04 | (2006.01) |
| G01N 33/52 | (2006.01) |
| C09K 11/06 | (2006.01) |
| C07D 311/16 | (2006.01) |
| C07D 409/04 | (2006.01) |

(52) U.S. Cl.
CPC ............ G01N 33/52 (2013.01); C07D 311/16 (2013.01); C07D 409/04 (2013.01); C09K 11/06 (2013.01); *C09K 2211/1088* (2013.01)

(58) Field of Classification Search
CPC .................................................. C07D 403/04
See application file for complete search history.

(56) References Cited

U.S. PATENT DOCUMENTS

| 3,501,490 A | 3/1970 | Maeder et al. |
| 3,966,755 A | 6/1976 | Schlapfer |
| 4,764,622 A | 8/1988 | Claussen et al. |
| 7,977,120 B2 | 7/2011 | Glass et al. |
| 2009/0011454 A1 | 1/2009 | Glass et al. |
| 2017/0082645 A1* | 3/2017 | Missouri ................ C09K 11/06 |

FOREIGN PATENT DOCUMENTS

| GB | 1010562 A | 11/1965 |
| GB | 1200852 A | 8/1970 |
| IN | 1306/MUM/2009 | 10/2009 |

OTHER PUBLICATIONS

American Chemical Society. STN Database. RN 152382-93-9. (c) Jan. 20, 1994.*
Li et al., "Coumarin-Derived Fluorescent Chemosensors", Advances in Chemical Sensors, 2012, pp. 121-150, Ch. 6.
Kitamura et al., "Synthesis, Absorption, and Fluorescence Properties and Crystal Structures of 7-Aminocoumarin Derivatives", Journal of Photochemisty and Photobiology A: Chemistry, 2007, pp. 378-386, vol. 188 No. 2.
Jagtap et al., "Synthesis of Highly Fluorescent Coumarinyl Chalcones Derived from 8-acetyl-1,4-diethyl-1,2,3,4-tetrahydro-7H-pyrano[2,3-g]quinoxalin-7-one and their Spectral Characteristics", Dyes and Pigments, Oct. 2011, pp. 20-25, vol. 91, Issue 11.
Jagtap et al., "The Synthesis and Characterization of Novel Coumarin Dyes Derived from 1,4-diethyl-1,2,3,4-tetrahydro-7-hydroxyquinoxalin-6-carboxaldehyde", Dyes and Pigments, Jul. 2009, pp. 84-89, vol. 82, Issue 1.

* cited by examiner

*Primary Examiner* — Andrew D Kosar
*Assistant Examiner* — John S Kenyon
(74) *Attorney, Agent, or Firm* — Thompson Coburn LLP; Steven M. Ritchey

(57) ABSTRACT

The invention is provides for a variety of fluorescence sensing compounds characterized generally as having a coumarin-3-aldehyde scaffold with a pendant aryl moiety at the C4-position of the scaffold. The further provides a method for detecting primary amines in a biological sample using said compounds. Especially, for the selective labeling and imaging of catecholamines in live and fixed secretory cells.

8 Claims, 17 Drawing Sheets

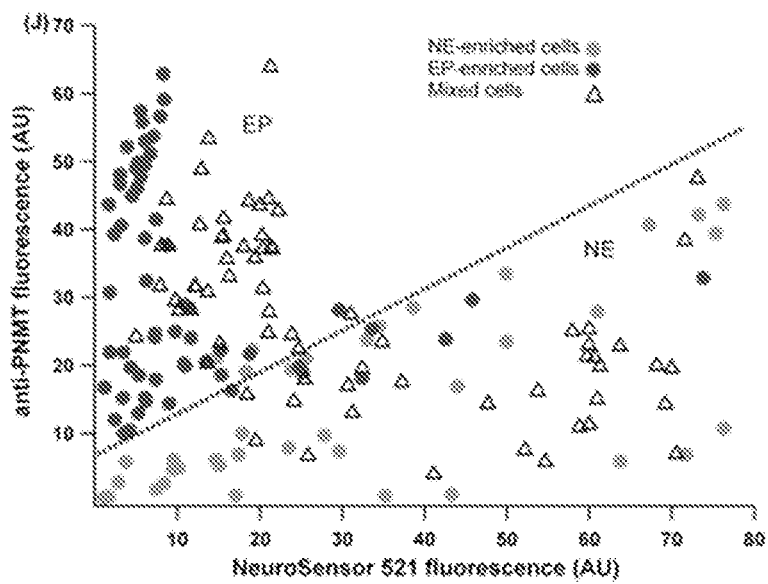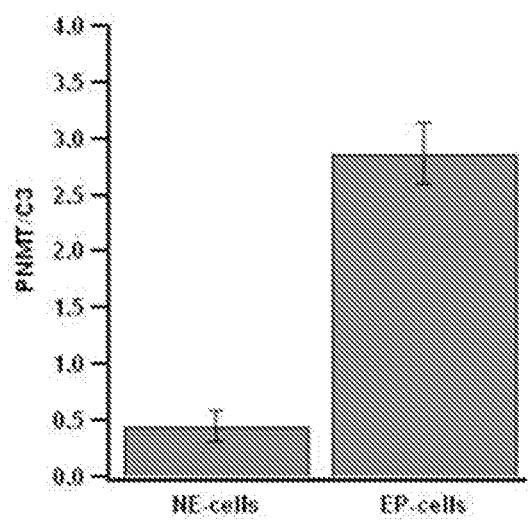
FIG. 9

Table 3. Association Constants ($K_a$) for the Binding of the Series I Sensors to Various Analytes[a]

| | Amine Guest | | | | | | |
|---|---|---|---|---|---|---|---|
| | Glutamate | | Norepinephrine | | Dopamine | | |
| Benzene-Based Moiety | $K_a$ (M$^{-1}$)[b] | $I_{sat}/I_0$[c] | $K_a$ (M$^{-1}$)[b] | $I_{sat}/I_0$[c] | $K_a$ (M$^{-1}$)[b] | $I_{sat}/I_0$[c] | |
| 4-Carbethoxy (1a) | 7.0 | 4.7 | 81.5 | 1.8 | 107.5 | 1.1 | |
| Phenyl (1b) | 9.4 | 10.5 | 68.7 | 6.6 | 68.1 | 3.3 | |
| 3-Methyl (1c) | 9.2 | 10.0 | 68.4 | 6.6 | 74.1 | 3.3 | |
| 4-Methylthio (1d) | 8.4 | 9.8 | 68.8 | 6.5 | 87.1 | 3.1 | |
| 4-Biphenyl (1e) | 13.8 | 6.2 | 148.8 | 2.6 | 203.3 | 1.6 | |
| 3-Fluoro-4-methoxy (1f) | 9.0 | 9.3 | 70.2 | 6.4 | 92.9 | 3.1 | |
| (NS521) 4-Methoxy (1g) | 9.6 | 7.8 | 77.8 | 5.4 | 112.1 | 3.0 | |
| Naphthalene (1h) | 10.1 | 6.8 | 103.7 | 4.3 | 170.0 | 2.9 | |
| 3,4-Dimethoxy (1i) | 10.2 | 6.6 | 107.2 | 4.1 | 177.5 | 2.7 | |
| 4-Methoxy-3-methyl (1j) | 10.3 | 6.4 | 136.0 | 3.9 | 192.1 | 2.4 | |
| 3,4,5-Trimethoxy (1k) | 10.3 | 5.0 | 159.1 | 2.6 | 203.1 | 1.6 | |
| 4-Dimethylamino (1l) | 10.2 | 1.7 | 160.0 | 1.2 | 206.2 | 1.1 | |

[a] Measured in buffer (1.0 μM sensor, 25 mM HEPES, 50 mM Na$_2$SO$_4$, pH = 5.0, 37 °C). [b] $K_a$ measured by fluorescence spectroscopy. Excited at 408 nm. [c] $I_{sat}$ = fluorescence intensity at saturation taken from the theoretical fit to a one-site binding isotherm. [d] Sensors 1a and 1e were adjusted to 5% and 30% DMSO, respectively.

Figure 20

Table 1. Association Constants ($K_a$) for the Binding of the Series 2 Sensors to Various Analytes[a]

| Thiophene-Based Moiety | Glutamate | | Amine Guest Norepinephrine | | Dopamine | |
|---|---|---|---|---|---|---|
| | $K_a$ (M$^{-1}$)[b] | $I_{\infty}/I_0$[c] | $K_a$ (M$^{-1}$)[b] | $I_{\infty}/I_0$[c] | $K_a$ (M$^{-1}$)[b] | $I_{\infty}/I_0$[c] |
| 2-Chlorothiophene (2a) | 5.9 | 34 | 69.2 | 21 | 84.0 | 12 |
| (NS530) Thiophene (2b) | 7.3 | 57 | 65.2 | 48 | 43.6 | 25 |
| 3-Methylthiophene (2c) | 7.4 | 51 | 63.6 | 38 | 51.1 | 23 |
| 2-Methylthiophene (2d) | 6.1 | 48 | 58.7 | 32 | 54.0 | 22 |
| Benzothiophene (2e) | 5.2 | 30 | 49.6 | 17 | 49.3 | 9.5 |

[a] Measured in buffer (5.0 μM sensor, 25 mM HEPES, 50 mM Na$_2$SO$_4$, pH = 5.0, 27 °C). [b] $K_a$ measured by fluorescence spectroscopy. Excited at 515 nm. [c] $I_{\infty}$ = fluorescence intensity at saturation taken from the theoretical fit to a one-site binding isotherm.

Figure 21

Table 5. Association Constants ($K_a$) for the Binding of the Series 1 Sensors to Various Analytes[a]

| Benzene-Based Moiety | Glutamate | | Norepinephrine | | Dopamine | |
|---|---|---|---|---|---|---|
| | $K_a$ (M$^{-1}$)[b] | $I_{sat}/I_0$[c] | $K_a$ (M$^{-1}$)[b] | $I_{sat}/I_0$[c] | $K_a$ (M$^{-1}$)[b] | $I_{sat}/I_0$[c] |
| 4-Carbethoxy (1a) | 7.0 | 4.7 | 81.5 | 1.8 | 107.5 | 1.1 |
| Phenyl (1b) | 9.4 | 10.5 | 68.7 | 6.6 | 68.1 | 3.2 |
| 3-Methyl (1c) | 9.2 | 10.0 | 69.4 | 6.6 | 74.1 | 3.2 |
| 4-Methylthio (1d) | 8.4 | 9.8 | 68.8 | 6.5 | 87.1 | 3.1 |
| 4-Biphenyl (1e) | 13.8 | 6.2 | 148.8 | 2.6 | 203.3 | 1.6 |
| 3-Fluoro-4-methoxy (1f) | 9.0 | 9.3 | 70.2 | 6.4 | 92.9 | 3.1 |
| (NS521) 4-Methoxy (1g) | 9.6 | 7.8 | 77.8 | 5.4 | 112.1 | 3.0 |
| Naphthalene (1h) | 10.1 | 6.8 | 103.7 | 4.3 | 170.0 | 2.9 |
| 3,4-Dimethoxy (1i) | 10.2 | 6.6 | 107.2 | 4.1 | 177.5 | 2.7 |
| 4-Methoxy-3-methyl (1j) | 10.3 | 6.4 | 136.0 | 3.9 | 192.1 | 2.4 |
| 3,4,5-Trimethoxy (1k) | 10.3 | 5.6 | 159.1 | 2.6 | 205.1 | 1.6 |
| 4-Dimethylamino (1l) | 10.2 | 1.7 | 160.0 | 1.2 | 206.2 | 1.1 |

[a]Measured in buffer (1.0 µM sensor, 25 mM HEPES, 50 mM Na$_2$S$_2$O$_3$, pH = 5.0, 37 °C). $K_a$ measured by fluorescence spectroscopy. Excited at 488 nm. [c]$I_{sat}$ = fluorescence intensity at saturation taken from the theoretical fit to a one-site binding isotherm. Sensors 1a and 1e were adjusted to 5% and 30% DMSO, respectively.

Figure 22

*Table 6.* Association Constants ($K_a$) for the Binding of the Series 2 Sensors to Various Analytes[a]

| Thiophene-Based Moiety | Glutamate | | Norepinephrine | | Dopamine | |
|---|---|---|---|---|---|---|
| | $K_a$ (M$^{-1}$)[b] | $I_{sat}/I_0$[c] | $K_a$ (M$^{-1}$)[b] | $I_{sat}/I_0$[c] | $K_a$ (M$^{-1}$)[b] | $I_{sat}/I_0$[c] |
| 2-Chlorothiophene (2a) | 5.9 | 34 | 69.2 | 21 | 84.0 | 12 |
| (NS539) Thiophene (2b) | 7.3 | 57 | 65.2 | 48 | 43.6 | 25 |
| 3-Methylthiophene (2c) | 7.4 | 51 | 63.6 | 38 | 51.1 | 23 |
| 2-Methylthiophene (2d) | 6.1 | 48 | 58.7 | 32 | 54.6 | 22 |
| Benzothiophene (2e) | 5.2 | 30 | 49.6 | 17 | 49.3 | 9.5 |

[a]Measured in buffer (5.0 μM sensor, 25 mM HEPES, 50 mM Na$_2$S$_2$O$_3$, pH = 5.0, 37 °C). [b]$K_a$ measured by fluorescence spectroscopy. Excited at 515 nm. [c]$I_{sat}$ = fluorescence intensity at saturation taken from the theoretical fit to a one-site binding isotherm.

Figure 23

Table 7. Calculated $E_{HOMO}$ and $E_{LUMO}$ Values for Select Neurotransmitters[a]
| Neurotransmitter | $E_{HOMO}$ | $E_{LUMO}$ |
|---|---|---|
|  Serotonin | -0.1890 | -0.0022 |
| 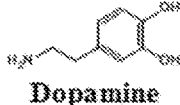 Dopamine | -0.2025 | -0.0028 |
| 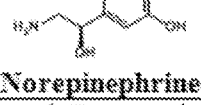 Norepinephrine | -0.2078 | -0.0082 |
[a] $E_{HOMO}$ and $E_{LUMO}$ values (hartrees) of the corresponding aryl moiety calculated with DFT B3LYP/6-31G(d) using Gaussian 09W Rev. A.02.
Figure 24

FLUORESCENT CHEMICAL SENSOR FOR BIOLOGICAL AMINES

CROSS REFERENCE TO RELATED APPLICATIONS

This application is a U.S. National Phase application of PCT/US2014/031490, filed on Mar. 21, 2014, which claims the benefit of US Provisional App No. 61/852,851, filed Mar. 21, 2013, both of which are incorporated herein by reference in their entireties.

GRANT STATEMENT

This invention was made with Government support under Grant No. 5R01GM059245 awarded by the National Institutes of Health. The Government has certain rights in the invention.

FIELD OF THE INVENTION

The present invention relates to fluorescent sensors for intracellular analyte detection. More particularly, the present invention relates to fluorescent sensors for selectively sensing amine-containing analytes.

BACKGROUND OF THE INVENTION

The catecholamines dopamine, norepinephrine, and epinephrine are the principal neurotransmitters in the sympathetic nervous system. In particular, norepinephrine regulates many critical functions that include attention, memory, learning, emotion, and autonomic and cardiovascular function. In the periphery, norepinephrine increases heart rate, cardiac contractility, vascular tone, renin-angiotensin system activity, and renal sodium reabsorption. Norepinephrine is secreted by chromaffin cells, which package catecholamines at high concentrations (0.5-1.0 M) and at low pH (5.0-5.5) in neurosecretory vesicles. Chromaffin cells possess approximately 30,000 large dense-core vesicles (LDCV) with norepinephrine and epinephrine. Chromaffin cells that store and release mainly epinephrine can be separated from those that utilize mainly norepinephrine through density-gradient centrifugation, though a third subpopulation which secrete both epinephrine and norepinephrine has been identified via cyclic voltametry. Over the years, chromaffin cells have become a standard platform for the study of processes related to exocytosis. Thus, chromaffin cells appeared to be an ideal platform for the study of novel sensors for neurotransmitters.

Currently, catecholamines can be studied via electrochemical and chromatographic techniques that provide characterization and quantification, although these techniques can only provide crude spatial information. Recently, fluorescent false neurotransmitters (FFNs) have been developed which are selectively loaded into vesicles that express neuronal vesicular monoamine transporter (VMAT) and represent an optical approach for labeling vesicles containing catecholamines and imaging catecholamine release at the single-vesicle level. However, FFNs are loaded into all secretory vesicles expressing the VMAT protein without discrimination to cell type and thus, the approach cannot distinguish distinct cell populations that secrete a particular neurotransmitter.

Fluorescent sensors remain a compelling technology for approaching the general problem of selective neurotransmitter detection. In recent years, a number of catecholamine sensors have been reported including RNA aptamers, fluorescent ribonucleopeptide (RNP) complexes, and boronic-acid based synthetic receptors. However, none of these methods represent a practical approach for in vivo and in vitro cellular analysis and imaging. Indeed, some time ago, the inventors developed a coumarin aldehyde fluorescent sensor,

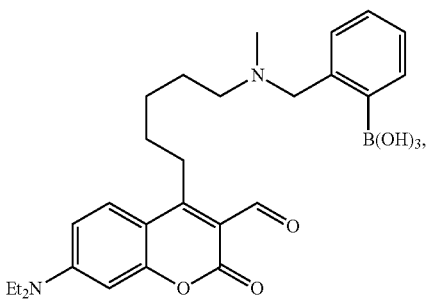

disclosed in U.S. Pat. No. 7,977,120 B2, for the selective recognition and sensing of amines. The '120 sensor, along with its derivatives, includes an aldehyde that associates with the analyte amine group via imine formation and a boronic acid that associates with the catechol group. Unfortunately, the catechol group strongly quenched the sensor. Thus, in the case of dopamine and norepinephrine, the sensor operated in a turn-off mode.

Therefore, there is a need for a series of fluorescence chemosensors to detect an organic primary-amine-containing analyte, such as, neurotransmitters and diamino-analytes, in a live cell. There is also a need for a series of fluorescence chemo sensors to operate in a turn-on mode when detecting dopamine and norepinephrine.

SUMMARY OF THE INVENTION

The present invention provides a series of fluorescent sensors that are highly fluorescent, effective, and selective in detecting primary-amine-containing analytes, such as, the neurotransmitters and the diamino-analytes in physiological conditions. The inventive sensor is designed with an aldehyde group to bind to all primary amines via iminium ion formation, but unlike the '120 sensor, without a boronic acid recognition unit to prevent being quenched by the catechol group.

More particularly, one embodiment of the present invention may be generally described as a fluorescence sensing compound that coumarin-3-aldehyde scaffold having a pendant aryl moiety at the C4-position of the scaffold. Still more particularly, said compound has the following formula:

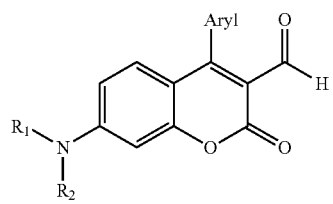

wherein

Aryl is an unsubstituted or substituted aryl moiety; and $R_1$ and $R_2$ are each independently selected from the group consisting of hydrogen, alkyl, alkylene, aryl, and cycloalkyl.

The present invention further provides a method of detecting primary-amine-containing analyte in a biological sample using aforesaid fluorescent sensing compounds. The inventive method comprises the steps of contacting the biological sample with a sensing compound described herein and detecting the presence of fluorescence in the sample, wherein the presence of fluorescence indicates the presence of a primary-amine in the sample.

BRIEF DESCRIPTION OF THE DRAWINGS

FIG. 7 b and d shows norepinephrine-containing cells incubated I-2 (0.1 μM): (b) λex=488 nm and (d) λex=440 nm.

FIG. 9: Quantification of cell fluorescence from the cell populations from FIG. 8. a) Fluorescence intensity at 585 nm plotted on the Y-axis and fluorescence intensity at 525 nm plotted on the X-axis. Each point represents an individual cell. EP-enriched cells fall above the blue line and NE-enriched cells fall below the blue line. b) The average ratio of fluorescence intensity at 585 nm vs. 525 for norepinephrine-enriched and epinephrine-enriched cells.

FIG. 20: Table 3.
FIG. 21: Table 4.
FIG. 22: Table 5.
FIG. 23: Table 6.
FIG. 24: Table 7

DETAILED DESCRIPTION OF THE INVENTION

Figure 1:
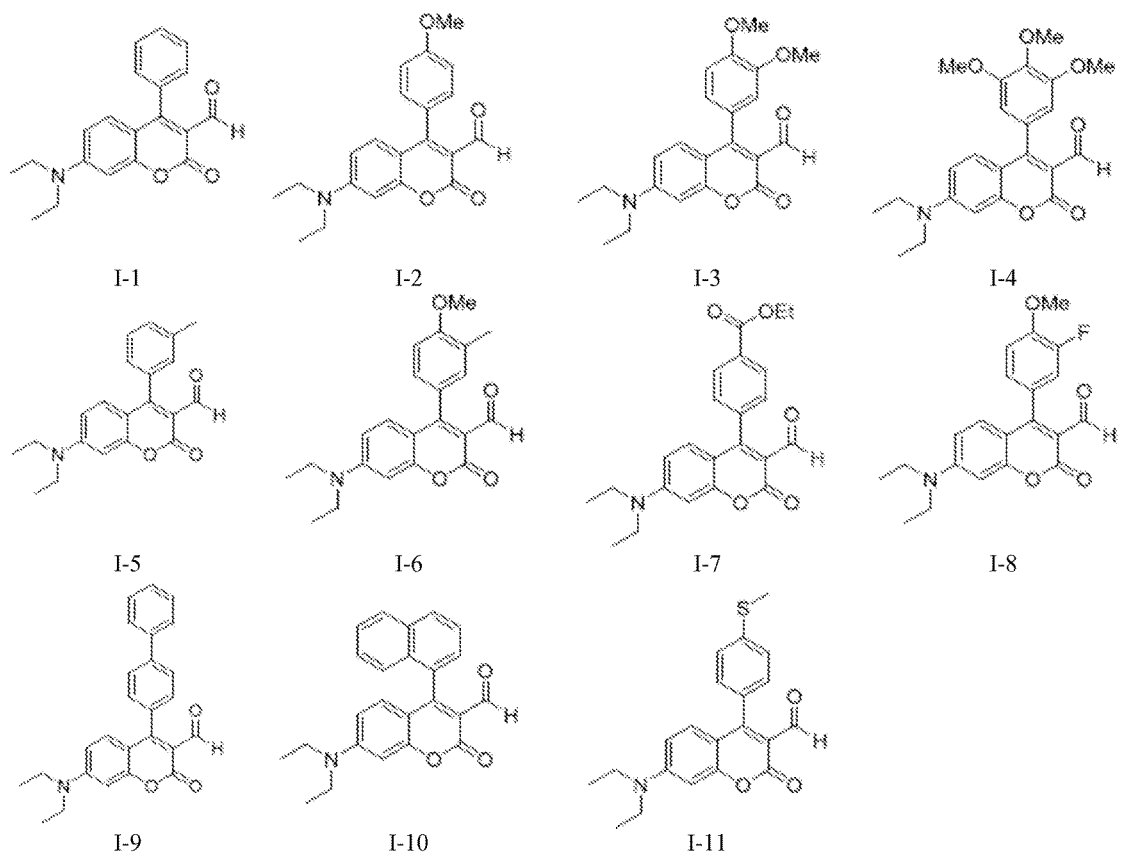
FIG. 1 illustrates the chemical structures of some representative fluorescent compound of formula I.

As indicated above, in one embodiment, the present invention is directed to a coumarin-3-aldehyde scaffold having a pendant aryl moiety at the C4-position of the scaffold. Still more particularly, said compound has the following formula:

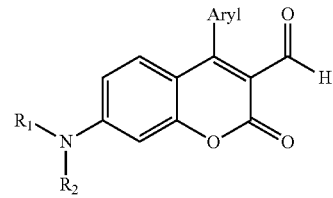

wherein

Aryl is an unsubstituted or substituted aryl moiety; and $R_1$ and $R_2$ are each independently selected from the group consisting of hydrogen, alkyl, alkylene, aryl, and cycloalkyl.

Of particular interest are aryl moieties that are benzene-based and heterocyclopentadiene-based having one or more heteroatoms selected from the group consisting of oxygen, sulfur, and nitrogen. These moieties may be monocylic or polycyclic and, if polycyclic, the rings may be homo- or hetero-cyclic. The benzene-based moiety and heterocyclopentadiene-based moiety are discussed in greater detail below.

Unless otherwise defined, all technical and scientific terms used herein have the same meaning as commonly understood by one of ordinary skill in the art to which this invention belongs. Throughout the specification and claims, a given chemical formula or name shall encompass all optical and stereoisomers as well as racemic mixtures where such isomers and mixtures exist.

B. Benzene-based Moiety

In one embodiment, the present invention is directed to a coumarin-aldehyde-and-phenyl-moiety-based fluorescence sensing compound of the Formula (I):

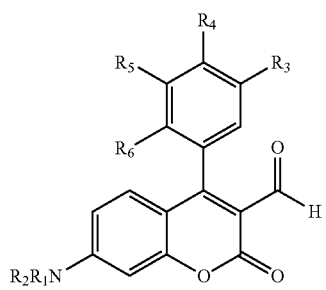

Formula (I)

wherein $R_1$ and $R_2$ are each independently hydrogen, alkyl, alkylene, aryl, or cycloalkyl; and $R_3$, $R_4$, $R_5$, and $R_6$ are each independently hydrogen, alkyl, alkylene, aryl, a constituent of a fused unsubstituted or substituted aryl, cycloalkyl, halo, hydroxyl, alkoxyl, aryloxy, alkylthio, or arylthio, carboxyl, or alkoxycarbonyl.

In various embodiments of the present invention, the benzene-based moiety has one of the following formulas:

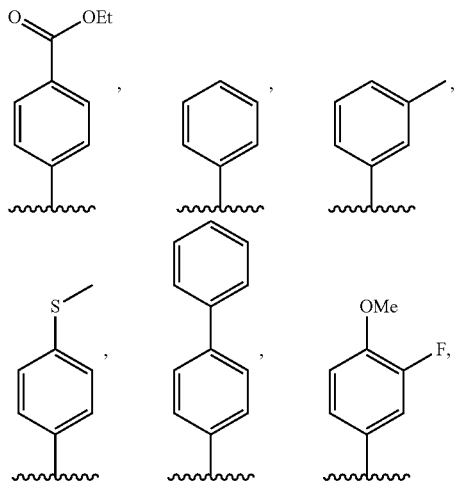

As shown in the foregoing formulas, one such moiety is naphthyl, a naphthalene-based moiety. As described in greater detail below, naphthalene-based moieties may be of particular interest. As such, in one embodiment the benzene-based moiety is a naphthalene-based moiety having the following formula:

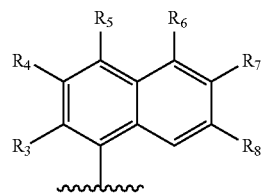

wherein $R_3$, $R_4$, $R_5$, $R_6$, $R_7$, and $R_8$ are each independently selected from the group consisting of hydrogen, alkyl, alkylene, aryl, a constituent of a fused unsubstituted or substituted aryl, cycloalkyl, halo, hydroxyl, alkoxyl, aryloxy, alkylthio, or arylthio, carboxyl, and alkoxycarbonyl.

C. Heterocyclonentadiene-based Moiety

Of particular interest are heterocyclopendtadiene-based moieties that are thiophene-based, furan-based, pyrrole-based, and azole-based.

1. Thionene-based Moiety

In one embodiment, the present invention is directed to a coumarin-aldehyde-and-thiophene-moiety-based fluorescence sensing compound of the Formula (II):

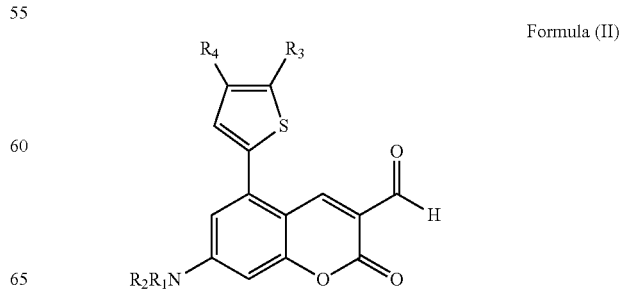

Formula (II)

wherein

R$_1$, and R$_2$ are each independently hydrogen, alkyl, alkylene, aryl, or cycloalkyl, and R$_3$ and R$_4$ are each independently hydrogen, alkyl, alkylene, aryl, cycloalkyl, halo, hydroxyl, alkoxyl, aryloxy, alkylthio, or arylthio, carboxyl, or alkoxycarbonyl, or R$_3$ and R$_4$ are each a constituent of a fused unsubstituted or substituted aryl.

In another embodiment, the thiophene-based moiety, wherein the thiophene-based moiety has the following formula:

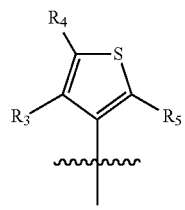

wherein R$_3$, R$_4$, and R$_5$ are each independently selected from the group consisting of hydrogen, alkyl, alkylene, aryl, cycloalkyl, halo, hydroxyl, alkoxyl, aryloxy, alkylthio, or arylthio, carboxyl, and alkoxycarbonyl, or R$_3$ and R$_4$ are each a constituent of a fused unsubstituted or substituted aryl.

In various embodiments of the present invention, the thiophene-based moiety has one of the following formulas:

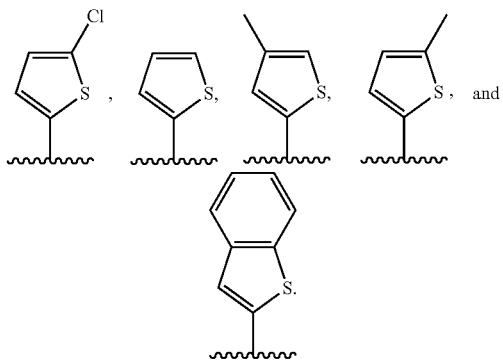

By "independently," the skilled artisan will appreciate that each and every group may be selected from the entire list set forth as possible selections without regard to the selections of other groups having the same or different appellations.

2. Furan-based Moiety

In one embodiment, the aryl moiety is a furan-based moiety, wherein the furan-based moiety has one of the following formulas:

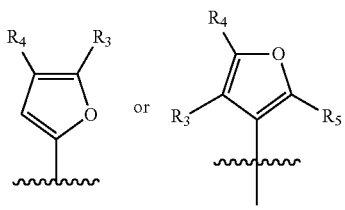

wherein R$_3$, R$_4$, and R$_5$ are each independently selected from the group consisting of hydrogen, alkyl, alkylene, aryl, cycloalkyl, halo, hydroxyl, alkoxyl, aryloxy, alkylthio, or arylthio, carboxyl, and alkoxycarbonyl, or R$_3$ and R$_4$ are each a constituent of a fused unsubstituted or substituted aryl.

In one embodiment the furan-based moiety has the following formula:

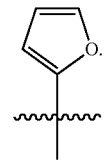

3. Pyrrole-based Moiety

In one embodiment, the aryl moiety is a pyrrole-based moiety, wherein the pyrrole-based moiety has one of the following formulas:

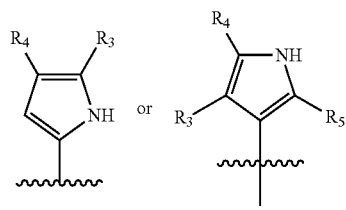

wherein R$_3$, R$_4$, and R$_5$ are each independently selected from the group consisting of hydrogen, alkyl, alkylene, aryl, cycloalkyl, halo, hydroxyl, alkoxyl, aryloxy, alkylthio, or arylthio, carboxyl, and alkoxycarbonyl, or R$_3$ and R$_4$ are each a constituent of a fused unsubstituted or substituted aryl.

In one embodiment, the pyrrole-based moiety has the following formula:

4. Azole-based Moiety

In one embodiment, the aryl moiety is the azole-based moiety, wherein the azole-based moiety has a has a formula selected from the group consisting of the following:

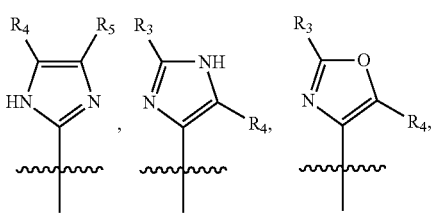

-continued

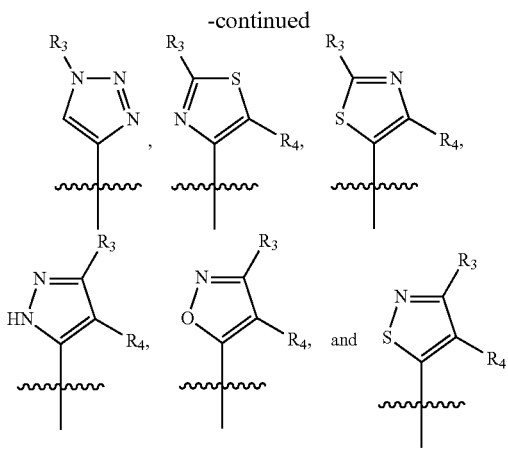

wherein $R_3$, $R_4$, and $R_5$, are each independently selected from the group consisting of hydrogen, alkyl, alkylene, aryl, cycloalkyl, halo, hydroxyl, alkoxyl, aryloxy, alkylthio, or arylthio, carboxyl, and alkoxycarbonyl.

In one embodiment, the azole-based moiety is a triazole moiety.

D. Terminology

As used herein the term "alkyl" refers to C1-10 inclusive, linear, branched, or cyclic, saturated or unsaturated (i.e., alkenyl and alkynyl) hydrocarbon chains. The alkyl group can be optionally substituted with one or more alkyl group substituents which can be the same or different, where "alkyl group substituent" includes alkyl, halo, arylamino, acyl, hydroxyl, aryloxy, alkoxyl, alkylthio, arylthio, aralkyloxy, aralkylthio, carboxy, alkoxycarbonyl, oxo and cycloalkyl. There can be optionally inserted along the alkyl chain one or more oxygen, sulfur or substituted nitrogen atoms, wherein the nitrogen substituent is hydrogen, lower alkyl (also referred to herein as "alkylaminoalkyl"), or aryl. "Branched" refers to an alkyl group in which a lower alkyl group, such as methyl, ethyl or propyl, is attached to linear alkyl chain.

"Aryl" refers to an aromatic substituent that may be a single ring or multiple rings that are fused together, linked covalently, or linked to a common group such as an ethylene, methylene or oxy moiety. The aromatic rings of the aryl group may each and optionally contain heteroatoms. The aryl group can be optionally substituted with one or more aryl group substituents which can be the same or different, where "aryl group substituent" includes alkyl, aryl, arylalkyl, hydroxy, alkoxyl, aryloxy, arylalkoxyl, carboxy, acyl, halo, nitro, alkoxycarbonyl, aryloxycarbonyl, arylalkoxycarbonyl, acyloxyl, acylamino, aroylamino, carbamoyl, alkylcarbamoyl, dialkylcarbamoyl, arylthio, alkylthio, alkylene and —NRR', where R and R' can be each independently hydrogen, alkyl, aryl and aralkyl.

As used herein, the terms "substituted alkyl" and "substituted aryl" include alkyl and aryl groups, as defined herein, in which one or more atoms or functional groups of the aryl or alkyl group are replaced with another atom or functional group, including for example, halogen, aryl, alkyl, alkoxyl, hydroxyl, nitro, amino, alkylamino, dialkylamino, sulfate, and mercapto.

"Cyclic" and "cycloalkyl" refer to a non-aromatic mono- or multicyclic ring system of about 3 to about 10 carbon atoms. The cycloalkyl group can be optionally partially unsaturated. The cycloalkyl group can be also optionally substituted with an alkyl group substituent as defined herein, ox and/or alkylene. There can be optionally inserted along the cyclic alkyl chain one or more oxygen, sulfur or substituted nitrogen atoms, wherein the nitrogen substituent is hydrogen, lower alkyl, or aryl, thus providing a heterocyclic group.

"Alkylene" refers to a straight or branched bivalent aliphatic hydrocarbon group having from 1 to about 10 carbon atoms. The alkylene group can be straight, branched or cyclic. The alkylene group can be also optionally unsaturated and/or substituted with one or more "alkyl group substituents." There can be optionally inserted along the alkylene group one or more oxygen, sulfur or substituted nitrogen atoms, wherein the nitrogen substituent is alkyl as previously described.

E. Additional Formula Diagrams

Figure 2:
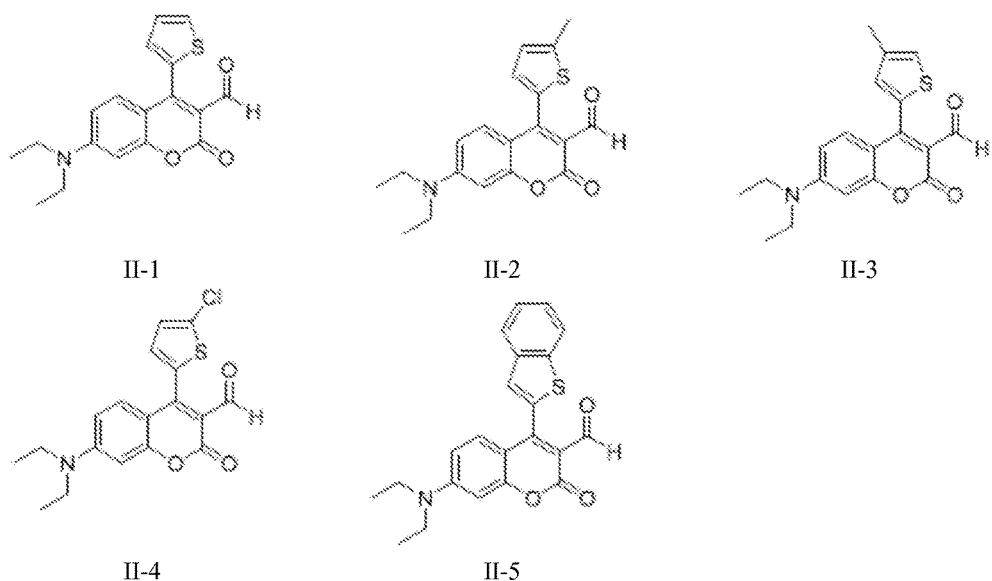
FIG. 2 illustrates the chemical structures of some representative fluorescent compound of formula II.

The invention also provides several exemplary embodiments of the sensing compounds of formula I and II. Refer to FIG. 1 and FIG. 2. The chemical structures of eleven exemplary embodiments of compound of formula I, I-1 to I-11, are illustrated in FIG. 1, while the chemical structures of five exemplary embodiments of compound of formula II, II-1 to II-5, are illustrated in FIG. 2.

F. Synthesis of Compounds

Figure 3:
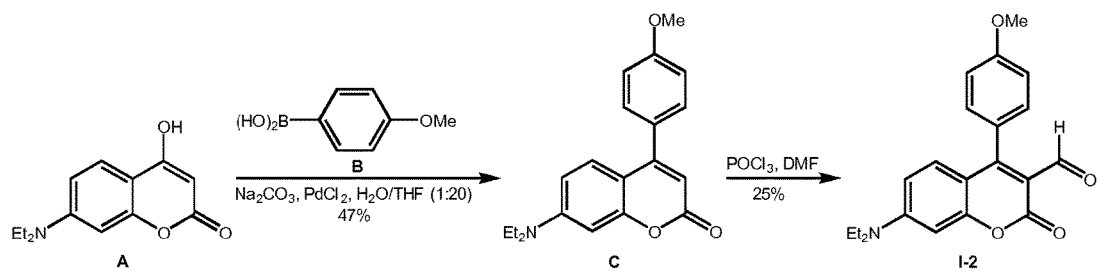
FIG. 3 illustrates the synthesis of the compound of formula I.

The invention further provides the general synthetic schemes for sensors of the present invention. For ease of discussion, the synthesis schemes will be directed to those of formula I and II. Refer to FIG. 3, which illustrates the synthetic scheme of the inventive sensor (I-2). As shown in FIG. 3, compound I-2 was prepared by a palladium catalyzed cross-coupling of the appropriate arylboronic acid to hydroxy coumarin A. The product C was formylated using standard Vilsmeyer conditions ($POCl_3$ in DMF) to produce sensor I-2. The detailed synthetic steps are further described in the Examples section below.

Figure 4:
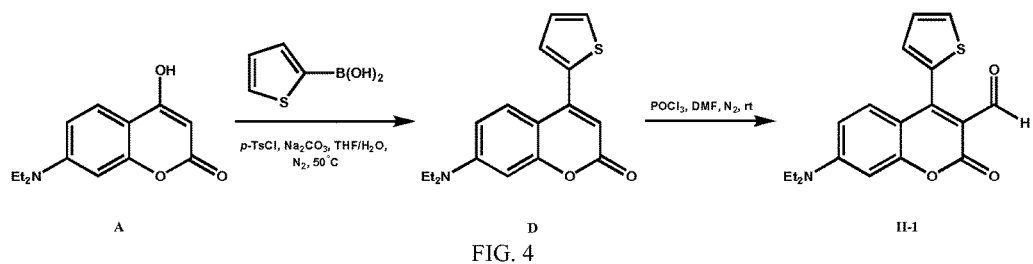
FIG. 4 illustrates the synthesis of the compound of formula II.

Refer to FIG. 4, which illustrates the general synthetic scheme of the inventive sensors (II). As shown in FIG. 4, compound II-1 was prepared by a palladium catalyzed cross-coupling of the appropriate thiophene boronic acid to hydroxy coumarin A. The product D was formylated using standard Vilsmeyer conditions ($POCl_3$ in DMF) to produce sensor II-1. This general synthesis is further described in the Examples section below, particularly in the synthesis of II-1.

G. Use of Compounds

The invention also provides for the use of the disclosed sensor compounds for selectively binding and thus detecting primary amine analytes. Comparing with '120 sensor, the inventive sensors are designed with the aldehyde group to associate with the analyte amines, while instead of a boronic acid group in '120 sensor, a phenyl or thiophene moiety is incorporated to modulate the fluorescence properties of the coumarin such that it cannot be quenched by the catechol group. It is believed that the lack of a boronic acid recognition unit may lower the affinity of the present sensor compounds for catecholamines relative to the '120 sensor, but given the extremely high concentration of catecholamine in the secretory vesicles, a lower binding constant is not a major concern.

Figure 5:
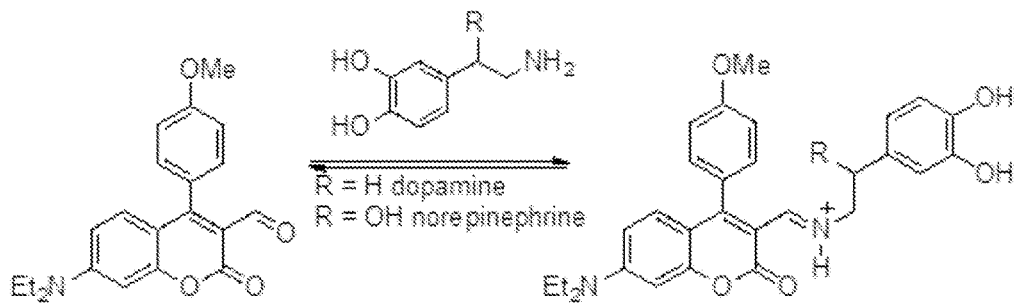
FIG. 5 illustrates the binding mechanism of compound I-2 and an exemplary primary amine.

Refer to FIG. 5, which illustrates the binding mechanism of the inventive sensors (represented by the exemplary I-2) with amine analytes. As shown in FIG. 5, the inventive sensor, I-2, binds to all primary amines via iminium ion formation.

Figure 6:
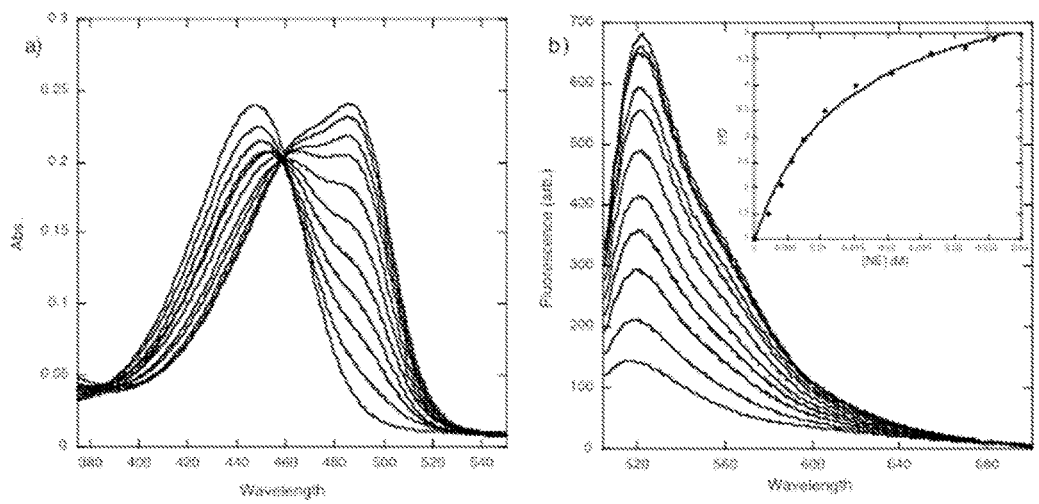
FIG. 6 illustrates titrations of I-2: a) UV/vis titration and b) fluorescence titration (10 μM in 25 mM HEPES, 50 mM $Na_2S_2O_3$, pH=5.0, 37° C.) with norepinephrine ($\lambda_{ex}$=488 nm). Inset in b) is the fit to a single-site binding isotherm.

Refer to FIG. 6, which includes a UV/vis titration and fluorescence titration of I-2 with norepinephrine. As shown in FIG. 6, I-2's binding with norepinephrine produces a red shift in absorption from 448 to 488 nm. In fluorescence mode, exciting the sensor at 488 nm and adding norepinephrine produced a marked 5.3-fold increase in fluorescence.

Table 1 summarizes binding and spectroscopic data for the interaction of I-2 and a number of relevant amines.

TABLE 1

Association Constants and Spectroscopic Parameters for the Binding of compound I-2 to Various Analytes

| Amine Guest | $K_a$ (M$^{-1}$)$^a$ | $I_{sat}/I_o$$^b$ ($\lambda_{ex}$ = 488 nm) | Quantum Yield ($\Phi$) |
|---|---|---|---|
| Epinephrine | 0 | nd | nd |
| Norepinephrine | 75 | 5.3 | 0.0033 |
| Dopamine | 112 | 3.0 | nd |
| Glutamate | 10 | 7.8 | 0.0095 |
| Lysine | 11 | 15.1 | nd |
| Glycine | 8 | 11.1 | nd |
| none | — | — | 0.0029 |

$^a$$K_a$ measured by fluorescence spectroscopy, $\lambda_{ex}$ = 488 nm, $\lambda_{em}$ = 521 nm. Error in $K_a$ values are ± 10% based on triplicate titrations.
$^b$$I_{sat}$ = fluorescence intensity at saturation taken from the theoretical fit to the binding isotherm.
nd = not determined.

As shown in Table 1, similarly to other sensors in this series, all primary amines bind with low binding affinity and high fluorescence enhancements. Interestingly, catacholamines such as norepinephrine and dopamine have 10-fold higher binding constants than other alkyl amines such as glycine. As with other sensors in the class, sensor I-2 does not interact with secondary amines such as epinephrine.

The data in Table 1 also indicates that the maximum fluorescence response of the catecholamines is lower than that of generic amines such as glutamate. The quantum yield for I-2 was determined both alone and bound to glutamate and norepinephrine. The three-fold difference in the latter two quantum yields is due to the quenching nature of the catechol group, which can undergo photoelectron transfer (PET) to the coumarin fluorophore. Taken together, these data suggest that I-2 will bind more strongly to catecholamines in a cell, but with lower overall fluorescent enhancements. In a neuroendocrine cell, the concentration of catecholamines (0.5-1.0 M) in secretory vesicles is at least an order of magnitude greater than the concentration of other biogenic primary amines. Thus, the moderate selectivity of I-2 (along with other compounds of formula I and II) for catecholamines over other biogenic amines coupled with the relatively high concentrations of catecholamines in secretory vesicles is expected to overcome the lower fluorescence response from the catecholamine. In addition, the unique spectral properties of I-2 allow for monitoring the unbound and bound states using the 440 nm versus 488 nm excitation, respectively.

The invention further teaches that the inventive sensors (I and II) may be employed in the selective detection of dopamine and norepinephrine over epinephrine in a cell. The detection method comprises the steps of contacting a biological sample containing amine analyte with a compound of formula I or II, and detecting the presence of fluorescence in the sample, wherein the presence of fluorescence indicates the presence of a primary-amine in the sample. The invention demonstrates, in EXAMPLES section, the utility of the detection method through the selective labeling and direct visualization of norepinephrine in secretory vesicles to distinguish norepinephrine- from epinephrine-enriched populations of chromaffin cells. Table 2 also summarizes binding and spectroscopic data for the interactions of several exemplary compounds of I and II and several relevant cellular amines.

TABLE 2

Interactions of Compounds I and II with Cellular Amines.

| | I-2 | | I-8 | | I-9 | | II-5 | |
|---|---|---|---|---|---|---|---|---|
| Analyte | $K_a$ (M$^{-1}$) | F.E. | $K_a$ (M$^{-1}$) | F.E. | $K_a$ (M$^{-1}$) | F.E. | $K_a$ (M$^{-1}$) | F.E. |
| Glutamate | 9.63 | 7.82 | 8.96 | 9.31 | 13.84 | 6.22 | 5.25 | 29.65 |
| Norepinephrine | 77.76 | 5.40 | 70.18 | 6.36 | 148.79 | 2.57 | 49.65 | 16.62 |
| Dopamine | 112.10 | 2.98 | 92.94 | 3.06 | 203.29 | 1.62 | 49.26 | 9.53 |

| | I-7 | | I-1 | | I-5 | | I-11 | |
|---|---|---|---|---|---|---|---|---|
| Analyte | $K_a$ (M$^{-1}$) | F.E. | $K_a$ (M$^{-1}$) | F.E. | $K_a$ (M$^{-1}$) | F.E. | $K_a$ (M$^{-1}$) | F.E. |
| Glutamate | 6.95 | 4.68 | 9.43 | 10.45 | 9.17 | 9.97 | 8.40 | 9.76 |
| Norepinephrine | 81.50 | 1.79 | 68.68 | 6.62 | 68.40 | 6.59 | 68.82 | 6.46 |
| Dopamine | 107.45 | 1.13 | 68.07 | 3.23 | 74.13 | 3.17 | 87.11 | 3.10 |

| | I-10 | | I-3 | | I-6 | | I-4 | |
|---|---|---|---|---|---|---|---|---|
| Analyte | $K_a$ (M$^{-1}$) | F.E. | $K_a$ (M$^{-1}$) | F.E. | $K_a$ (M$^{-1}$) | F.E. | $K_a$ (M$^{-1}$) | F.E. |
| Glutamate | 10.08 | 6.81 | 10.21 | 6.56 | 10.25 | 6.36 | 10.25 | 5.57 |
| Norepinephrine | 103.56 | 4.30 | 107.17 | 4.11 | 135.98 | 3.89 | 159.08 | 2.56 |
| Dopamine | 170.10 | 2.86 | 177.46 | 2.69 | 192.05 | 2.41 | 205.13 | 1.62 |

| | II-4 | | II-1 | | II-3 | | II-2 | |
|---|---|---|---|---|---|---|---|---|
| Analyte | $K_a$ (M$^{-1}$) | F.E. | $K_a$ (M$^{-1}$) | F.E. | $K_a$ (M$^{-1}$) | F.E. | $K_a$ (M$^{-1}$) | F.E. |
| Glutamate | 5.90 | 33.96 | 7.32 | 57.17 | 7.40 | 51.15 | 6.11 | 47.67 |
| Norepinephrine | 69.25 | 20.78 | 65.15 | 47.95 | 63.65 | 38.35 | 58.72 | 32.35 |
| Dopamine | 83.96 | 12.39 | 43.55 | 25.42 | 51.10 | 23.41 | 54.61 | 22.18 |

EXAMPLES (A) Example 1 Synthesis of Compound I (1) Synthesis of Compound I-2

(a) 7-diethylamino-4-(4'-methoxyphenyl)coumarin (C)

Compound A (250.0 mg, 1.072 mmol), p-toluenesulfonyl chloride (224.8 mg, 1.179 mmol), and $Na_2CO_3$ (340.8 mg, 3.215 mmol) were added to a flame-dried round bottom and degassed with $N_2$ for 15 minutes. Degassed $H_2O$/THF (1:20, 15.0 mL) was added and the mixture stirred at 50° C. for 30 minutes. The mixture was allowed to cool to room temperature. 4-Methoxyphenylboronic acid B (179.2 mg, 1.179 mmol) was added and the mixture was allowed to stir at room temperature for 5 minutes. Palladium chloride (9.5 mg, 0.054 mmol) was added and the mixture stirred at 50° C. for 6 hours. The mixture was filtered and the solvent removed in vacuo. The remaining residue was purified by chromatography (100% $CH_2Cl_2 \rightarrow$ 95:5 $CH_2Cl_2$/EtOAc) to yield compound C (172 mg, 47%) as a pale-yellow oil: $^1$H NMR (500 MHz, $CDCl_3$) δ 7.40 (dd, 2H, J=6.0, 1.0), 7.32 (dd, 1H, J=8.8, 1.0), 7.02 (dd, 2H, J=7.8, 1.5), 6.57 (d, 1H, J=2.0), 6.53 (dd, 1H, J=9.3, 2.0), 6.00 (d, 1H, J=1.0), 3.88 (s, 3H), 3.42 (q, 4H, J=7.0), 1.21 (t, 6H, J=7.0); $^{13}$C NMR (125 MHz, $CDCl_3$) δ 162.3, 160.5, 156.8, 150.5, 129.8, 128.5, 127.9, 114.0, 108.4, 108.0, 107.9, 97.8, 55.4, 44.7, 12.4; IR (neat, $cm^{-1}$) 2970, 1712, 1614, 1524, 1417, 1246, 1115, 829; HRMS calculated for $C_{20}H_{21}NO_3Na^+$ ($M+Na^+$): 346.1414. Found: 346.1415.

(b) 7-diethylamino-3-formyl-4-(4'-methoxyphenyl)coumarin (I-2)

$POCl_3$ (5.2 mL, 56.1 mmol) was added to DMF (10.8 mL, 139.5 mmol) at 0° C. in a flame-dried round bottom flask. The Vilsmeier reagent was stirred at ambient temperature for 45 minutes. The Vilsmeier reagent (5 mL) was added to a solution of compound C (171.8 mg, 0.532 mmol) in DMF (1 mL). The solution was stirred at ambient temperature for 12 hours. The resulting red solution was poured onto cold $H_2O$ (100 mL), basified with saturated $NaHCO_3$ (50 mL), and extracted with $CH_2Cl_2$ (100 mL×3). The combined organic layers were dried over $Na_2SO_4$ and the solvent was removed in vacuo. The residue was purified by chromatography (80:20 hexanes:EtOAc→50:50 hexanes/EtOAc) to yield I-2 (46.1 mg, 25%) as a yellow oil: $^1$H NMR (500 MHz, d-acetone) δ 9.80 (s, 1H), 7.27 (dd, 2H, J=2.0, 6.5), 7.08 (dd, 2H, J=2.0, 6.5), 6.99 (d, 1H, J=9.5), 6.71 (dd, 1H, J=2.5, 9.5), 6.55 (d, 1H, J=2.5), 3.89 (s, 3H), 3.56 (q, 4H, J=7.0), 1.22 (t, 6H, J=7.0); $^{13}$C NMR (125 MHz, d-acetone) δ 188.0, 161.8, 161.2, 160.0, 158.7, 153.9, 131.7, 131.0, 126.2, 114.5, 113.2, 110.6, 109.8, 97.5, 55.7, 45.5, 12.7; IR (neat, $cm^{-1}$) 2970, 2919, 2846, 1742, 1615, 1495, 1418, 1356, 1248, 1132; HRMS calculated for $C_{21}H_{21}NO_4Na^+$ ($M+Na^+$): 374.1363. Found: 374.1364.

(2) Data for Compound I-1

$^1$H NMR (500 MHz, $CD_2Cl_2$) δ 9.78 (s, 1H), 7.47-7.55 (m, 3H), 7.23-7.30 (m, 2H), 6.93 (d, 1H, J=10.0 Hz), 6.50-6.57 (m, 2H), 3.45 (q, 4H, J=7.0 Hz), 1.23 (t, 6H, J=7.0 Hz); $^{13}$C NMR (125 MHz, $CD_2Cl_2$) δ 188.4, 162.0, 159.9, 158.1, 153.4, 133.7, 131.2, 129.3, 128.8, 128.7, 112.7, 110.2, 109.5, 97.4, 45.6, 12.5; IR (neat, $cm^{-1}$) 2974, 1751, 1715, 1683, 1617, 1559, 1504, 1418, 1354; HRMS calculated for $C_{20}H_{19}NO_3$ ($M+Na^+$): 344.1257. Found: 344.1254.

(3) Data for Compound I-3

$^1$H NMR (500 MHz, $CDCl_3$) δ 9.82 (s, 1H), 7.08 (d, 1H, J=9.0 Hz), 7.00 (d, 1H, J=8.0 Hz), 6.87 (dd, 1H, J=8.0, 2.0 Hz), 6.80 (d, 1H, J=1.5 Hz), 6.50-6.55 (m, 2H), 3.97 (s, 3H), 3.88 (s, 3H), 3.46 (q, 4H, J=7.0 Hz), 1.25 (t, 6H, J=7.0 Hz); $^{13}$C NMR (125 MHz, $CDCl_3$) δ 188.5, 162.2, 159.4, 157.7, 153.0, 149.8, 148.9, 130.9, 125.0, 121.6, 112.6, 111.9, 110.9, 109.6, 109.1, 97.1, 56.1, 56.0, 45.2, 12.4; IR (neat, $cm^{-1}$) 2974, 1736, 1650, 1615, 1506, 1455, 1377, 1168; HRMS calculated for $C_{22}H_{23}NO_5$ ($M+Na^+$): 404.1468. Found: 404.1465.

(4) Data for Compound I-4

$^1$H NMR (500 MHz, $CDCl_3$) δ 9.81 (s, 1H), 7.08 (d, 1H, J=9.0 Hz), 6.55 (dd, 1H, J=9.0, 2.5 Hz), 6.52 (d, 1H, J=2.5 Hz), 6.51 (s, 2H), 3.94 (s, 3H), 3.86 (s, 6H), 3.46 (q, 4H, J=7.0 Hz), 1.24 (t, 6H, J=7.0 Hz); $^{13}$C NMR (125 MHz, $CDCl_3$) δ 188.3, 162.3, 159.1, 157.7, 153.4, 138.5, 130.8, 128.2, 112.4, 109.7, 108.8, 105.9, 97.0, 61.1, 56.3, 45.2, 12.4; IR (neat, $cm^{-1}$) 1748, 1618, 1495, 1417, 1352, 1123; HRMS calculated for $C_{23}H_{25}NO_6$ ($M+Na^+$): 434.1574. Found: 434.1570.

(5) Data for Compound I-5

$^1$H NMR (500 MHz, $CDCl_3$) δ 9.79 (s, 1H), 7.39 (t, 1H, J=8.0 Hz), 7.31 (d, 1H, J=8.0 Hz), 7.06-7.09 (m, 2H), 6.98 (d, 1H, J=10.0 Hz), 6.48-6.53 (m, 2H), 3.43 (q, 4H, J=7.0 Hz), 2.42 (s, 3H), 1.22 (t, 6H, J=7.0 Hz); $^{13}$C NMR (125 MHz, $CDCl_3$) δ 188.4, 162.6, 159.4, 157.7, 153.0, 138.2, 132.8, 131.0, 129.9, 129.0, 128.3, 125.6, 112.3, 109.6, 109.0, 97.0, 45.1, 21.4, 12.4; IR (neat, $cm^{-1}$) 1744, 1712, 1614, 1556, 1503, 1417, 1352, 1127, 730.

(6) Data for Compound I-6

$^1$H NMR (500 MHz, $CDCl_3$) δ 9.75 (s, 1H), 7.03-7.10 (m, 3H), 6.91 (d, 1H, J=8.5 Hz), 6.50 (dd, 1H, J=8.5, 2.0 Hz), 6.48 (d, 1H, J=2.0 Hz), 3.89 (s, 3H), 3.43 (q, 4H, J=7.0 Hz), 2.25 (s, 3H), 1.21 (t, 6H, J=7.0 Hz); 13C NMR (125 MHz, CDCl3) δ 188.6, 162.8, 159.2, 158.6, 157.6, 152.9, 131.1, 130.9, 127.8, 126.8, 124.0, 112.5, 109.5, 109.4, 109.0, 96.9, 55.4, 45.1, 16.2, 12.4; IR (neat, cm-1) 1746, 1611, 1511, 1495, 1419, 1353, 1251, 1137.

(7) Data for Compound I-7

$^1$H NMR (500 MHz, CDCl3) δ 9.95 (s, 1H), 8.18 (d, 2H, J=8.0 Hz), 7.32 (d, 2H, J=8.5 Hz), 6.84 (d, 1H, J=9.0 Hz), 6.52 (d, 1H, J=2.5 Hz), 6.49 (dd, 1H, J=9.0, 2.5 Hz), 4.43 (q, 2H, J=7.0 Hz), 3.45 (q, 4H, J=7.5 Hz), 1.43 (t, 3H, J=7.0 Hz), 1.23 (t, 6H, J=7.0 Hz); 13C NMR (125 MHz, CDCl3) δ 188.0, 166.0, 160.5, 159.7, 157.8, 153.1, 138.3, 130.9, 130.8, 129.6, 128.1, 111.7, 109.9, 108.8, 97.1, 61.2, 45.2, 14.3, 12.4; IR (neat, cm-1) 2978, 1716, 1614, 1556, 1499, 1356, 1270, 1127, 1103, 727; HRMS calculated for C23H23NO5 (M+Na+): 416.1468. Found: 416.1464.

(8) Data for Compound I-8

$^1$H NMR (500 MHz, CDCl3) δ 9.91 (s, 1H), 7.09 (t, 1H, J=8.5 Hz), 6.98-7.03 (m, 3H), 6.49-6.55 (m, 2H), 3.98 (s, 3H), 3.46 (q, 4H, J=7.0 Hz), 1.22 (t, 6H, J=7.0 Hz); 13C NMR (125 MHz, CDCl3) δ 188.2, 160.1, 159.8, 157.8, 153.0, 152.9, 151.0, 148.4, 148.3, 130.8, 125.5, 125.4, 124.8, 116.7, 116.5, 113.2, 113.1, 112.2, 109.8, 109.0, 97.1, 56.3, 45.2, 12.4; IR (neat, cm-1) 1747, 1614, 1556, 1520, 1499, 1429, 1417, 1354, 1270, 1136.

(9) Data for Compound I-9

$^1$H NMR (500 MHz, $CDCl_3$) δ 9.92 (s, 1H), 7.74 (d, 2H, J=8.5 Hz), 7.68 (d, 2H, J=8.0 Hz), 7.50 (t, 2H, J=7.5 Hz), 7.42 (t, 1H, J=7.5 Hz), 7.36 (d, 2H, J=8.0 Hz), 7.06 (d, 1H, J=9.5 Hz), 6.51-6.56 (m, 2H), 3.45 (q, 4H, J=7.5 Hz), 1.26 (t, 6H, J=7.5 Hz); $^{13}$C NMR (125 MHz, $CDCl_3$) δ 188.4, 161.7, 159.8, 157.8, 153.1, 142.0, 140.1, 131.9, 131.0, 129.0, 128.9, 127.8, 127.2, 127.1, 112.4, 109.7, 109.1, 97.1, 45.2, 12.4; IR (neat, $cm^{-1}$) 1745, 1711, 1610, 1558, 1498, 1419, 1352, 1131.

(10) Data for Compound I-10

$^1$H NMR (500 MHz, $CDCl_3$) δ 9.72 (s, 1H), 7.98 (d, 1H, J=8.5 Hz), 7.94 (dd, 1H, J=8.5, 1.5 Hz), 7.58 (t, 1H, J=7.5 Hz), 7.48-7.54 (m, 2H), 7.41 (td, 1H, J=8.0, 1.0 Hz), 7.34

(dd, 1H, J=7.0, 1.0 Hz), 6.70 (d, 1H, J=9.0), 6.55 (d, 1H, J=2.5 Hz), 6.37 (dd, 1H, J=9.5, 2.5 Hz), 3.42 (q, 4H, J=7.0 Hz), 1.21 (t, 6H, J=7.0 Hz); $^{13}$C NMR (125 MHz, CDCl$_3$) δ 188.0, 161.1, 159.7, 153.2, 133.2, 131.1, 131.0, 130.9, 129.3, 128.5, 127.1, 126.5, 126.0, 125.1, 125.0, 113.3, 109.8, 109.5, 96.9, 45.2, 12.4; IR (neat, cm$^{-1}$) 1744, 1716, 1679, 1614, 1552, 1499, 1417, 1352, 1136.

(11) Data for Compound I-11

$^1$H NMR (500 MHz, CDCl$_3$) δ 9.88 (s, 1H), 7.36 (d, 2H, J=8.5 Hz), 7.20 (d, 2H, J=8.5 Hz), 7.01 (d, 1H, J=8.0 Hz), 6.48-6.52 (m, 2H), 3.45 (q, 4H, J=7.0 Hz), 2.56 (s, 3H), 1.24 (t, 6H, J=7.0); $^{13}$C NMR (125 MHz, CDCl$_3$) δ 188.3, 161.3, 159.9, 157.8, 153.0, 140.5, 130.9, 129.3, 129.0, 125.7, 112.3, 109.6, 109.0, 97.1, 45.2, 15.3, 12.4; IR (neat, cm$^{-1}$) 1746, 1714, 1612, 1558, 1507, 1487, 1420, 1353, 1132.

(B) Example 2. Synthesis of Compound II (1) Synthesis of Compound II-1

(a) Compound D

Compound A (250.0 mg, 1.072 mmol), p-toluenesulfonyl chloride (224.8 mg, 1.179 mmol), and Na$_2$CO$_3$ (340.8 mg, 3.215 mmol) were added to a flame-dried round bottom and degassed with N$_2$ for 15 minutes. Degassed H$_2$O/THF (1:20, 15.0 mL) was added and the mixture stirred at 50° C. for 30 minutes. The mixture was allowed to cool to room temperature. Thiophene or substituted thiopheneboronic acid (1.179 mmol) was added to the mixture and was allowed to stir at room temperature for 5 minutes. Palladium chloride (9.5 mg, 0.054 mmol) was added and the mixture stirred at 50° C. for 6 hours. The mixture was filtered and the solvent removed in vacuo. The remaining residue was purified by chromatography (100% CH$_2$Cl$_2$→95:5 CH$_2$Cl$_2$/EtOAc). The material was further purified by chromatography (90:10 hexanes/EtOAc→50:50 hexanes/EtOAc) to yield the desired compound as a pale yellow oil. Compound D: $^1$H NMR (500 MHz, CDCl$_3$) δ 7.69 (d, 1H, J=8.5 Hz), 7.51 (dd, 1H, J=5.5, 0.5 Hz), 7.39 (dd, 1H, J=3.5, 0.5 Hz), 7.18-7.21 (m, 1H), 6.55-6.61 (m, 2H), 6.15 (s, 1H), 3.44 (q, 4H, J=7.0 Hz), 1.23 (t, 6H, J=7.0 Hz); $^{13}$C NMR (125 MHz, CDCl$_3$) δ 161.8, 156.8, 15.7, 148.2, 137.2, 128.6, 127.8, 127.7, 127.6, 108.6, 108.2, 107.1, 98.0, 44.8, 12.4; IR (neat, cm$^{-1}$) 3101, 2974, 1704, 1614, 1430, 1405, 1352, 1274, 1107; HRMS calculated for C$_{17}$H$_{17}$NO$_2$S (M+Na$^+$): 322.0872.

(b) Compound II-1

POCl$_3$ (5.2 mL, 56.1 mmol) was added to DMF (10.8 mL, 139.5 mmol) at 0° C. in a flame-dried round bottom flask. The Vilsmeier reagent was stirred at ambient temperature for 45 min. The Vilsmeier reagent (5 mL) was added to a solution of 4-thiophene-substituted-7-diethylaminocoumarin in DMF (1 mL). The solution was stirred at ambient temperature for 12 hours. The resulting red solution was poured onto cold H$_2$O (100 mL), basified with saturated NaHCO$_3$ (50 mL), and extracted with CH$_2$Cl$_2$ (100 mL×3). The combined organic layers were dried over Na$_2$SO$_4$ and the solvent was removed in vacuo. The residue was purified by chromatography (90:10 hexanes:EtOAc→50:50 hexanes/EtOAc) to yield the desired formylated compound as a yellow oil. Compound II-1:

$^1$H NMR (500 MHz, CD$_2$Cl$_2$) δ 9.84 (s, 1H), 7.64 (dd, 1H, J=5.0, 1.0 Hz), 7.20-7.25 (m, 2H), 7.16 (dd, 1H, J=4.0, 1.0 Hz), 6.60 (dd, 1H, J=9.0, 2.5 Hz), 6.53 (d, 1H, J=2.5 Hz), 3.46 (q, 4H, J=7.5 Hz), 1.23 (t, 6H, J=7.5 Hz); $^{13}$C NMR (125 MHz, CD$_2$Cl$_2$) δ 188.0, 159.2, 157.9, 155.0, 153.5, 132.7, 130.9, 130.2, 128.7, 127.7, 114.0, 110.4, 109.8, 97.5, 45.7, 12.6; IR (neat, cm$^{-1}$) 2921, 1740, 1614, 1495, 1442, 1417, 1356; HRMS calculated for C$_{18}$H$_{17}$NO$_3$S (M+Na$^+$): 350.0821. Found: 350.0818.

(2) Data for Compound II-2

$^1$H NMR (500 MHz, CDCl$_3$) δ 9.92 (s, 1H), 7.41 (d, 1H, J=9.5 Hz), 6.99 (d, 1H, J=3.5 Hz), 6.88 (dd, 1H, J=3.5, 1.0 Hz), 6.58 (dd, 1H, J=9.0, 2.5 Hz), 6.52 (d, 1H, J=2.5 Hz), 3.48 (q, 4H, J=7.0 Hz), 2.61 (s, 3H), 1.26 (t, 6H, J=7.0 Hz); $^{13}$C NMR (125 MHz, CDCl$_3$) δ 188.1, 158.9, 157.5, 155.2, 153.0, 144.0, 130.7, 130.5, 129.5, 125.8, 113.5, 109.6, 109.1, 97.1, 45.2, 15.3, 12.5; IR (neat, cm$^{-1}$) 1744, 1610, 1561, 1499, 1422, 1266, 1123; HRMS calculated for C$_{19}$H$_{19}$NO$_3$S (M+Na$^+$): 364.0978. Found: 364.0975.

(3) Data for Compound II-3

Yield 72%; $^1$H NMR (500 MHz, CDCl$_3$) δ 9.89 (s, 1H), 7.34 (d, 1H, J=8.5 Hz), 7.19 (s, 1H), 6.97 (s, 1H), 6.57 (dd, 1H, J=9.0, 2.5 Hz), 6.50 (d, 1H, J=2.5 Hz), 3.46 (q, 4H, J=7.0 Hz), 2.36 (s, 3H), 1.25 (t, 6H, J=7.0 Hz); $^{13}$C NMR (125 MHz, CDCl$_3$) δ 188.0, 158.8, 157.5, 155.3, 153.1, 138.1, 132.3, 131.8, 130.6, 124.0, 113.5, 109.7, 109.1, 97.1, 45.2, 15.6, 12.5; IR (neat, cm$^{-1}$) 2966, 1748, 1712, 1610, 1438, 1373, 1270, 1070, 731; HRMS calculated for C$_{19}$H$_{19}$NO$_3$S (M+Na$^+$): 364.097785. Found: 364.097734.

(4) Data for Compound II-4

$^1$H NMR (500 MHz, CDCl$_3$) δ 10.00 (s, 1H), 7.30 (d, 1H, J=9.5 Hz), 7.02 (d, 1H, J=4.0 Hz), 6.89 (d, 1H, J=4.0 Hz), 6.57 (dd, 1H, J=9.0, 2.5), 6.49 (d, 1H, J=2.5 Hz), 3.47 (q, 4H, J=7.0 Hz), 1.24 (t, 6H, J=7.0 Hz); $^{13}$C NMR (125 MHz, CDCl$_3$) δ 187.7, 159.6, 157.5, 153.2, 152.4, 133.1, 131.1, 130.5, 128.8, 126.4, 113.2, 110.0, 109.1, 97.1, 45.2, 12.4; IR (neat, cm$^{-1}$) 2970, 1748, 1717, 1611, 1559, 1499, 1439, 1412; HRMS calculated for C$_{18}$H$_{16}$ClNO$_3$S (M+Na$^+$): 384.0432. Found: 384.0432.

(5) Data for Compound II-5

$^1$H NMR (500 MHz, CDCl$_3$) δ 9.99 (s, 1H), 7.88 (dd, 1H, J=8.5, 1.5 Hz), 7.85 (dd, 1H, J=7.0, 2.0 Hz), 7.40-7.48 (m, 2H), 7.35 (s, 1H), 7.29 (d, 1H, J=9.0 Hz), 6.50-6.56 (2H), 3.46 (q, 4H, J=7.0 Hz), 1.24 (t, 6H, J=7.0 Hz); $^{13}$C NMR (125 MHz, CDCl$_3$) δ 187.7, 159.2, 157.5, 154.3, 153.2, 140.7, 139.2, 132.9, 130.7, 126.1, 125.3, 125.0, 124.2, 122.2, 113.2, 109.9, 109.0, 97.0, 45.2, 12.4; IR (neat, cm$^{-1}$) 1742, 1615, 1491, 1418, 1356, 1268, 1148, 723.

(C) Example 3—Selective Labeling and Direct Visualization of Norepinephrine in Chromaffin Cells with Compound I-2

Chromaffin cells were separated into norepinephrine-enriched and epinephrine-enriched fractions by centrifugation on a Percoll gradient. Both populations were independently incubated with a 0.1 μM solution of Compound I-2 at 37° C. for 30 minutes and then washed to remove excess sensor and plated.

Figure 7:
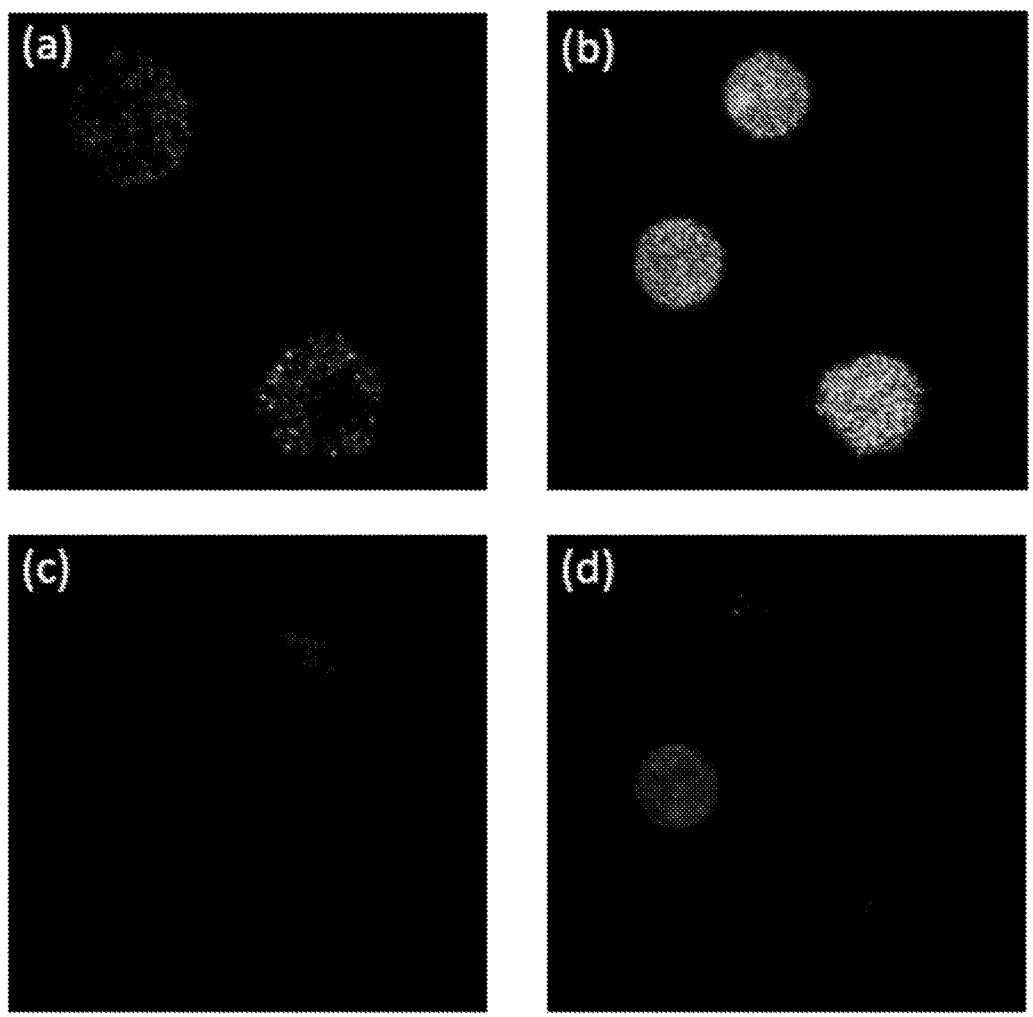
FIG. 7 a and c show epinephrine-containing cells incubated with I-2 (0.1 μM): (a) λex=488 nm and (c) λex=440 nm.

Refer to FIG. 7(a,b), whereas the cells were examined by confocal fluorescence microscopy using 488 nm excitation. The norepinephrine-enriched cell population showed strong, punctate fluorescence compared to the epinephrine-enriched cell population, which only showed marginal fluorescence. The punctate fluorescence pattern is consistent with secretory vesicles in chromaffin cells.

Refer to FIG. 7(c,d), whereas the cells were excited at 440 nm to selectively excite any potential unbound sensor. No significant fluorescence was observed in either the epinephrine- or norepinephrine-enriched cell populations. The data suggest that Compound I-2 resides predominantly in its bound state in the norepinephrine-enriched cells.

These results indicate that the inventive sensor is able to enter the vesicle and bind to norepinephrine selectively over epinephrine, as anticipated. The low fluorescence response observed within the epinephrine-containing chromaffin cells was attributed to the binding of I-2 to the low concentration of norepinephrine present in these vesicles. The lack of significant fluorescence upon excitation at 440 nm indicates that the majority of the sensor is in its bound state. This result supports that Compound I-2 accumulates in vesicles, which is not surprising for a neutral compound that forms a charged complex upon interaction with the target analyte. The charged complex presumably cannot cross the vesicle membrane and thus becomes trapped. Thus, the higher fluorescence in the norepinephrine-containing cells is a result of the high concentration of primary catecholamine in the vesicles, which causes accumulation of the sensor in these vesicles. Lacking significant concentrations of primary catecholamines, the epinephrine-containing cells do not accumulate the sensor and show lower fluorescence. The overall low background fluorescence is remarkable given the rather promiscuous binding of Compound I-2 to primary amines. Here the rather low affinity of the sensor for binding amines actually confers an advantage for selective labeling of high concentrations of primary amine analytes in secretory vesicles.

To further validate the selectivity of the inventive sensor, the inventive detection method is validated with an established procedure in which phenylethanolamine N-methyltransferase (PNMT) is stained with an antibody and visualized with a Cy3-conjugated secondary antibody. It has been shown that epinephrine-enriched cell populations gave the highest level of PNMT staining, while norepinephrine-enriched populations gave lower staining (ca. 20% of that with epinephrine-enriched cells). For this experiment, three populations of chromaffin cells (norepinephrine-enriched, epin ephrine-enriched, and mixed) were stained with Compound I-2 and fixed in 4% paraformaldehyde. The fixed cells were stained with the anti-PNMT and secondary antibodies.

Figure 8:
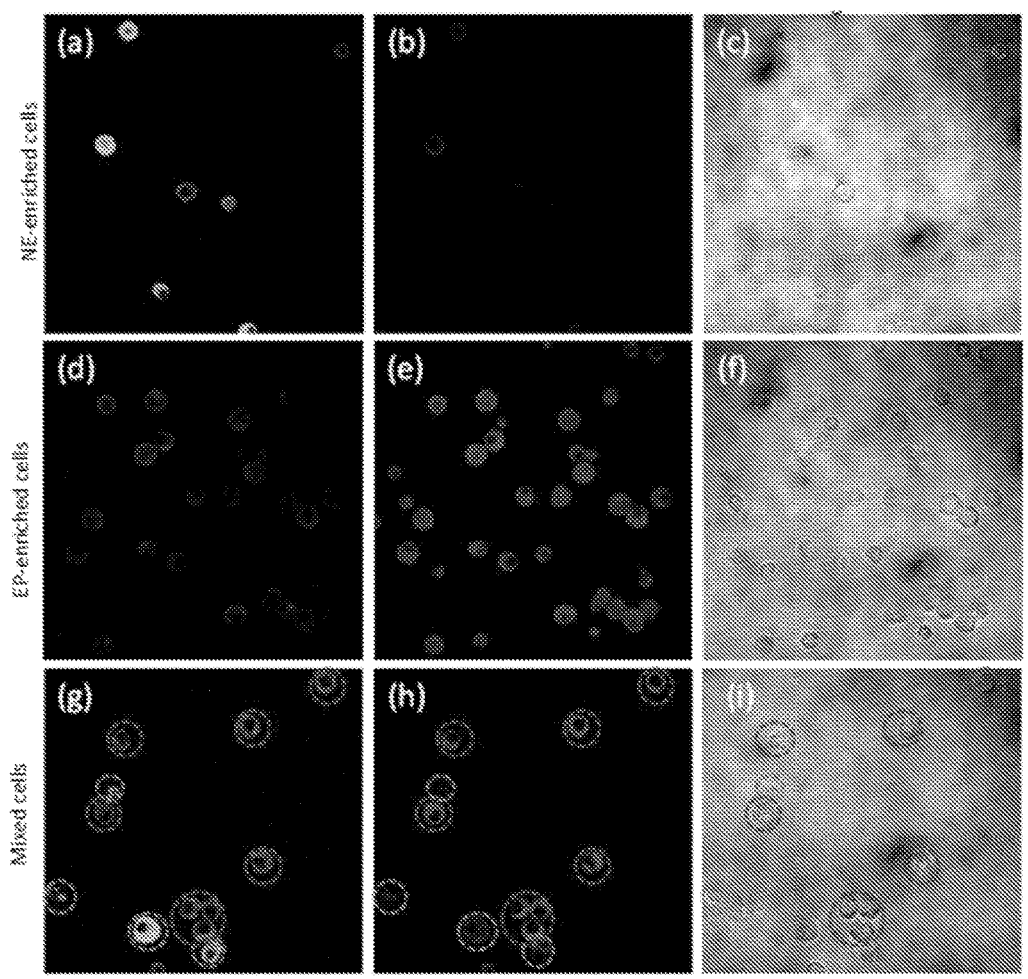
FIG. 8: All cells were stained with I-2 (1 μM), fixed (4% formaldehyde), and incubated with an anti-PNMT antibody followed by a Cy3-anti-rabbit antibody. Norepinephrine-enriched cells (a, b, and c) visualized at (a) 525 nm, (b) 585 nm and (c) bright field. Epinephrine-enriched cells (d, e, and f) visualized at (d) 525 nm (e) 585 nm and (f) bright field. Mixed cells (g, h, i) visualized at (g) 525 nm, (h) 585 nm and (i) bright field. Cells circled in light gray indicate NE-enriched cells and cells circled in medium dark gray indicated EP-enriched cells.

Refer to FIG. 8. The top row shows that the NE-enriched population of cells stain brightly with I-2 and weakly with the fluorescent antibody while the opposite is true for the EP-enriched cell population (second row). Indeed the mixed population of cells (third row) contained cells with staining patterns consistent with both NE-enriched cells (circled in light gray) and EP-enriched cells (circled in medium dark gray).

Refer to FIG. 9, whereas the fluorescence emission in the images shown in FIG. 8 were quantified using ImageJ. As shown in FIG. 9a, EP-enriched cells show an increased anti-PNMT staining compared to I-2. Conversely, the NE-enriched cells showed an increased staining by I-2 compared to the anit-PNMT. The mixed cell population contained cells which fell into both categories as expected. The average fluorescence intensity at 585 nm vs. 525 for epinephrine-enriched cells was 6 times of that of norepinephrine-enriched cells (FIG. 9b).

(D) Methods for Examples 1-3

(1) Fluorescence Titrations

Fluorescence spectra were recorded on a Shimadzu RF-5301 PC spectrofluorometer at 37° C. A 1 mg/mL stock solution of I-2 in DMSO was prepared. A stock solution of I-2 in buffer ($1\times10^{-5}$ M, 25 mM HEPES, 50 mM $Na_2S_2O_3$, pH=5.0) was prepared. Norepinephrine, dopamine, epinephrine, and glutamate stock solutions were prepared by separately dissolving the analytes at the concentration to be used in the titration with the buffered stock solution of I-2 (thus avoiding dilution of I-2 during the experiment). I-2 was titrated with aliquots of analyte solution. The sensor was excited at 488 nm with slit widths of 5 nm.

(2) Chromaffin Cells Preparation

Chromaffin cells were isolated from bovine adrenal glands as previously described. Following centrifugation at 18° C. at 13,000 rpm for 45 minutes in the Percoll gradient, chromaffin cells separate into fractions enriched with either epinephrine-enriched cells (denser band) and norepineph-rine-enriched cells (lighter band). Moro, M. A.; López, M. G.; Gandía, L.; Michelena, P.; Garcia, G. Separation and culture of living adrenaline- and noradrenaline-containing cells from bovine adrenal medullae. Anal. Biochem. 1990, 185, 243-248. Over 90% of the catecholamine content found in the cells in the denser fraction are epinephrine, whereas approximately 67% of the catecholamine content in the lighter fraction are norepinephrine. Liu, X.; Barizuddin, S.; Shin, W.; Mathai, C. J.; Gangopadhyay, S.; Gillis, K. D. Microwell device for targeting single cells to electrochemical microelectrodes for high-throughput amperometric detection of quantal exocytosis. Anal. Chem. 2011, 83, 2445-2451. The two cell fractions were collected from the Percoll gradient with careful pipetting and separately cultured. An alternative culture method was used to make it easier to detach the cells from the flasks and to reduce cell clumping. Chromaffin cells were cultured in Hibernate A media with calcium (BrainBits LLC, Springfield, Ill., USA) in a refrigerator (4° C.) and used 1-6 days after preparation. Id.

(3) Standard Cell Bath Solution

The standard cell bath solution for live-cell imaging consisted of 150 mM NaCl, 5 mM KCl, 2 mM $CaCl_2$, 1.2 mM $MgCl_2$, 10 mM HEPES, and 11 mM glucose titrated to pH 7.2 with 1 M NaOH.

(4) Live Cells Experiments

Approximately 5 mL of culture media containing suspended norepinephrine cells or epinephrine cells were centrifuged at 1000 rpm for 5 minutes. The pellet was re-suspended in 1 mL Dulbecco's Modified Eagles Medium (DMEM). Next, the cells were incubated on a 35 mm Petri dish with either 0.1 μM (for live cells experiments) or 1 μM sensor (for fixed cells experiments) in a humidified incubator at 37° C. with 5% $CO_2$ for 30 minutes. Norepinephrine cells or epinephrine cells were transferred into 15 mL conical tubes, spun, and washed twice with pre-warmed PBS (DPBS, Gibco, Invitrogen, Grand Island, N.Y., USA). Next, the cells were re-suspended in pre-warmed chromaffin cell regular medium (DMEM supplemented with 10% (v/v) fetal bovine serum and 1% penicillin/streptomycin). The cells were plated onto 0.0025% poly-L-lysine coated coverslips within 35 mm Petri dishes and incubated at 37° C. with 5% $CO_2$ for 10 minutes to promote cell adhesion to the coverslips. The coverslip with norepinephrine cells or epinephrine cells was mounted onto the stage of Olympus Optical FluoView FV1000 Confocal Laser Scanning Biological Microscope. A standard cell bath solution was added and the images were acquired using a laser with a wavelength of either 488 nm or 440 nm.

(5) Fixed Cells Experiments

NE-enriched cells, EP-enriched cells and mixed cells stained with I-2 (1 μM) and plated on 0.0025% Poly (1-lysine) coated cover slips, after three washed with pre-warmed phosphate-buffered saline (pH=7.4, PBS), were fixed in 4% paraformaldehyde (Sigma, St. Louis, Mo., USA) in PBS for 60 min at room temperature (RT), followed by 6 min in methanol chilled to −20° C. Cells were incubated at 4° C. with anti-PNMT antibody (1:1000 dilution, Millipore, Temecula, Calif., 92590) in PBS with 3% BSA and 0.1% Triton X-100. Cahill, A. L.; Eertmoed, A. L.; Mangoura, D.; Perlman, R. L. Differential regulation of phenylethanolamine N-methyltransferase expression in two distinct subpopulations of bovine chromaffin cells. J. Neurochem. 1996, 67, 1217-1224. After three washed in PBS, bound antibody was detected using Cy™3-conjugated AffiniPure Donkey Anti-Rabbit (1:150 dilution, Jackson ImmunoResearch Laboratories, Inc, Nest Grove, Pa., 19390). Cells were finally washed three times with PBS. NE-enriched cells, EP-enriched cells and mixed cells on the coverslips were mounted onto the stage of Olympus Optical Fluoview FV1000 Confocal Laser Scanning Biological Microscope, then prolong gold antifade mounting medium (Invitrogen, Eugene, Oreg.) was added and the images were acquired. Excitation and emission wavelength, 488 nm and Qdot525 was used for I-2, while 559 nm and Qdot585 was used for PNMT.

Figure 10:
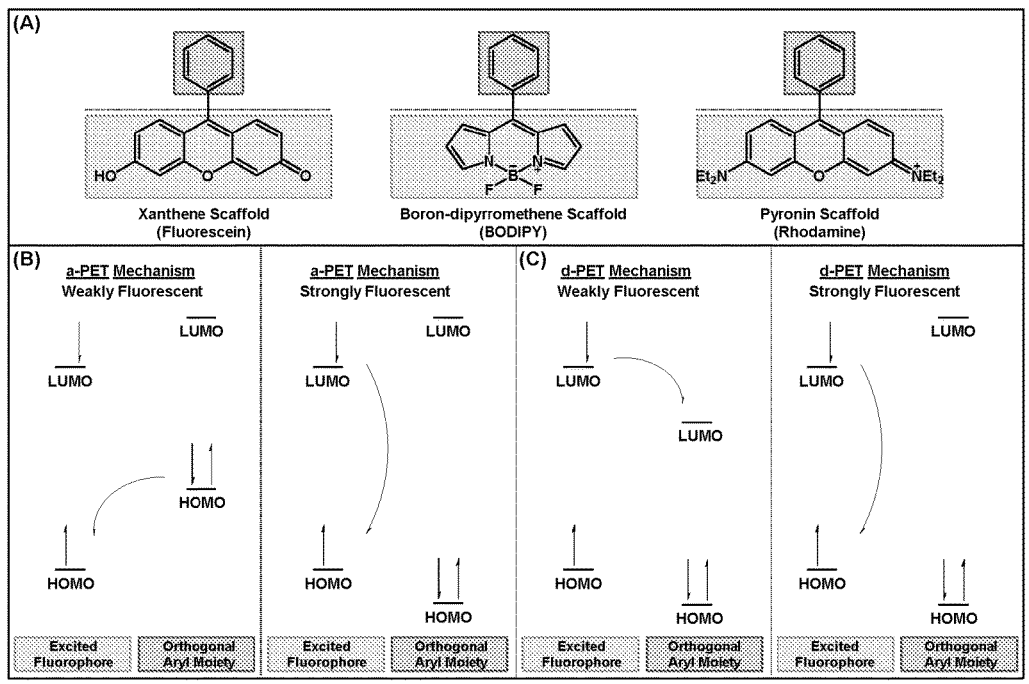
FIG. 10: (A) Platforms that consist of a directly linked donor-acceptor system which exhibit intramolecular PET between an orthogonal pendant aryl moiety and an excited state fluorophore (scaffold). (B) Frontier orbital energy level diagram for an acceptor-excited PET (a-PET) mechanism. (C) Frontier orbital energy level diagram for a donor-excited PET (d-PET) mechanism.

(E) Example 4—Coumarin-3-Aldehyde as a Scaffold for the Design of Tunable PET-Modulated Fluorescent Sensors for Neurotransmitters Fluorescence imaging, in its many forms, has become the premier method for unraveling complex biological problems. A variety of probes are available for fluorescent labeling of macromolecules; however, small molecule imaging often requires the use of fluorescent chemical sensors. An important goal in this field remains the ability to rationally design fluorescent probes and sensors. Recently, it has been shown that several fluorophores act as directly linked donor-acceptor systems (FIG. 10A) in which a pendant aryl moiety that is orthogonal to and not conjugated with the fluorophore can modulate the fluorescence output by intramolecular photoinduced electron transfer (PET). This PET quenching can occur in either a donor- or acceptor-excited mechanism (FIG. 10B, C), and balancing the electronics of the system is key to obtaining the desired fluorescence properties.

To describe these systems in a quantitative fashion, the rate of electron transfer ($k_{ET}$) between the excited state fluorophore (scaffold) and the pendant aryl moiety was determined from the free energy change for electron transfer ($\Delta G_{ET}$) using the Marcus equation. In turn, $\Delta G_{ET}$ values were determined from the Rehm-Weller equation using experimentally measured oxidation and reduction potentials of the platform components. The data could then be used to calculate the fluorescence quantum yields ($\Phi_{fl}$) of the derivatives. Most importantly, it has been demonstrated that there is a direct relationship between the experimentally determined quantum yield and the calculated energy of the highest occupied molecular orbital ($E_{HOMO}$) of the corresponding pendant aryl moiety. This relationship greatly facilitates the a priori determination of fluorescence output. However, to be truly quantitative, it was necessary to have experimentally determined oxidation potential of the unsubstituted scaffolds (fluorophores). Thus, only the xanthene and BODIPY scaffolds have undergone quantitative evaluation. However, the method has been used for qualitative assessment of fluorescence properties based on platforms consisting of modified scaffolds.

Figure 11:
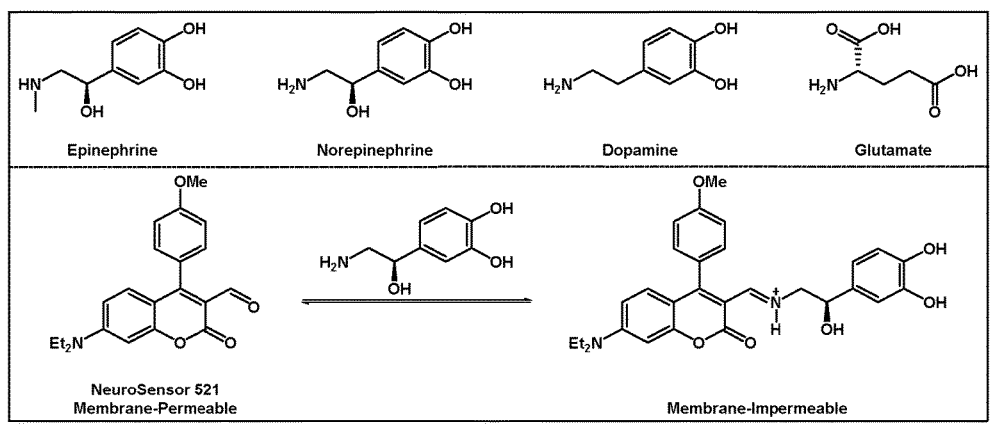
FIG. 11: Structures of select neurotransmitters. Structure of NS521 and formation of the iminium ion upon interaction with norepinephrine.

As mentioned above, the '120 sensor (a ditopic fluorescent molecular sensor that exhibited good selectivity toward catecholamines) operated in a turn-off mode due to quenching of the fluorophore by the catechol group. In contrast, NeuroSensor 521 (NS521), which corresponds to compound I-2 and compound 1g disclosed herein, operates as a turn-on fluorescent sensor for the catecholamines norepinephrine and dopamine (FIG. 11).

NS521 derives from the coumarin-3-aldehyde scaffold, wherein the aldehyde group associates with the analyte primary amine group via reversible iminium ion formation. The coumarin aldehyde fluoresces from an internal charge transfer (ICT) state. Formation of the iminium ion stabilizes the ICT state and shifts the wavelength of absorbance from 448 nm to 488 nm, allowing the bound and unbound forms of the sensor to be independently monitored by appropriate selection of the excitation wavelength. In principle, the aldehyde group of NS521 can interact with any intracellular free primary amine. However, the low binding affinities of NS521 toward free primary amines (~10 $M^{-1}$) coupled with the low concentration of intracellular free primary amines (5 mM) translates into extremely weak associations and thus, NS521 remains largely unassociated upon exposure to typical cells. However, specialized neurons sequester and package individual primary-amine neurotransmitters (e.g., glutamate, norepinephrine, dopamine, and serotonin) in secretory vesicles at extremely high concentrations (300 mM-1 M) within an acidic environment (~pH 5). It is envisaged that the neutral NS521 would diffuse into the secretory vesicles of such specialized cells and only bind with the primary amine neurotransmitter due to the extremely high concentration of the bioanalyte. In turn, the resultant imine form of NS521 would become protonated to form a charged complex due to the acidic environment within secretory vesicles and become membrane-impermeable (FIG. 11). As a result, the sensor would accumulate inside the secretory vesicles and allow for clear visualization of the neurotransmitter with low background. NS521 was initially validated in chromaffin cells and demonstrated selective detection of norepinephrine, allowing discrimination between norepinephrine- and epinephrine-enriched cell populations.

While NS521 was validated with norepinephrine, it also responds well to dopamine. Since the fluorescent imaging of neurons, neurotransmitters, and events surrounding synaptic firing is an increasingly active area of research, the potential applications of such sensors are profuse. Fluorescent sensors would enable research in neuroscience by providing both the imaging of primary-amine neurotransmitters (especially for neurotransmitters such as dopamine that tend to quench fluorescence) and the continuous monitoring of primary-amine neurotransmitter trafficking. Therefore, it was desirable to develop a model by which sensors could be rationally designed for the purposes of neuroimaging. As such, various NS521 analogues were prepared and investigated to evaluate the photophysical interaction between the platform components.

In particular, the above-described benzene- and thiophene-substituted sensors were prepared and investigated. The photophysical properties, binding affinities, and fluorescence responses toward glutamate, norepinephrine, and dopamine, were experimentally determined. DFT calculations provided the energy of the highest occupied molecular orbital ($E_{HOMO}$) values of the pendant aryl substituents (calculated at the B3LYP/6-31G(d) level of theory), which were fine-tuned through the introduction of various electron-withdrawing and -donating groups. In conjunction with the Marcus theory of electron transfer, oxidation and reduction potential values strictly derived from the calculated molecular orbital energy values of the fluorophores allowed for calculation of the fluorescence properties of the sensors. Good agreement between the calculated and experimentally determined fluorescence properties was found only in the case of the benzene-substituted sensors.

(1) Results
(a) Design and Synthesis of NS521 Derivatives

To systematically investigate the directly linked intramolecular PET in this system, a series of benzene- and thiophene-substituted derivatives based on the coumarin-3-aldehyde scaffold were prepared (FIG. 12A). Substituents on the C4 aryl groups were chosen to cover a wide range of calculated $E_{HOMO}$ values (FIG. 12B). The primary difference between the two classes of aryl moieties is the dihedral angle of the pendant aryl moiety with respect to the plane of the coumarin aldehyde scaffold. The thiophene class was determined to maintain a smaller dihedral angle (72.1°) compared to the benzene class (82.3°) based on geometry-optimized structures. For the purpose of discussion, it is noted that the only ortho-substituted derivative (1h) was determined to have a larger dihedral angle (89.3°).

Figure 13:
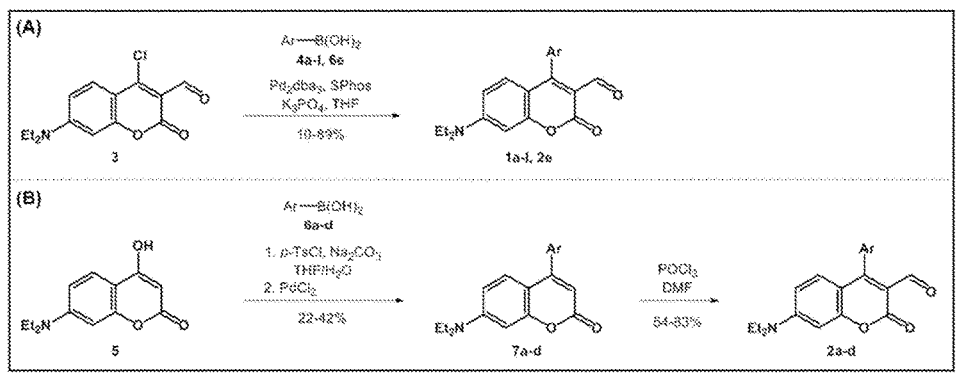
FIG. 13: Synthesis of (A) benzene- and (B) thiophene-substituted sensors based on the coumarin-3-aldehyde scaffold.

The sensors were prepared as shown in FIG. 13. The synthesis of the benzene-based sensors (1a-1) and the benzothiophene sensor (2e) was achieved through a single Suzuki coupling reaction with compound 3 to provide the final products. The thiophene-based sensors (2a-d) were synthesized in two steps from compound 5, via tosylation and coupling followed by formylation under Vilsmeier conditions.

(b) Spectroscopic Properties

Figure 14:
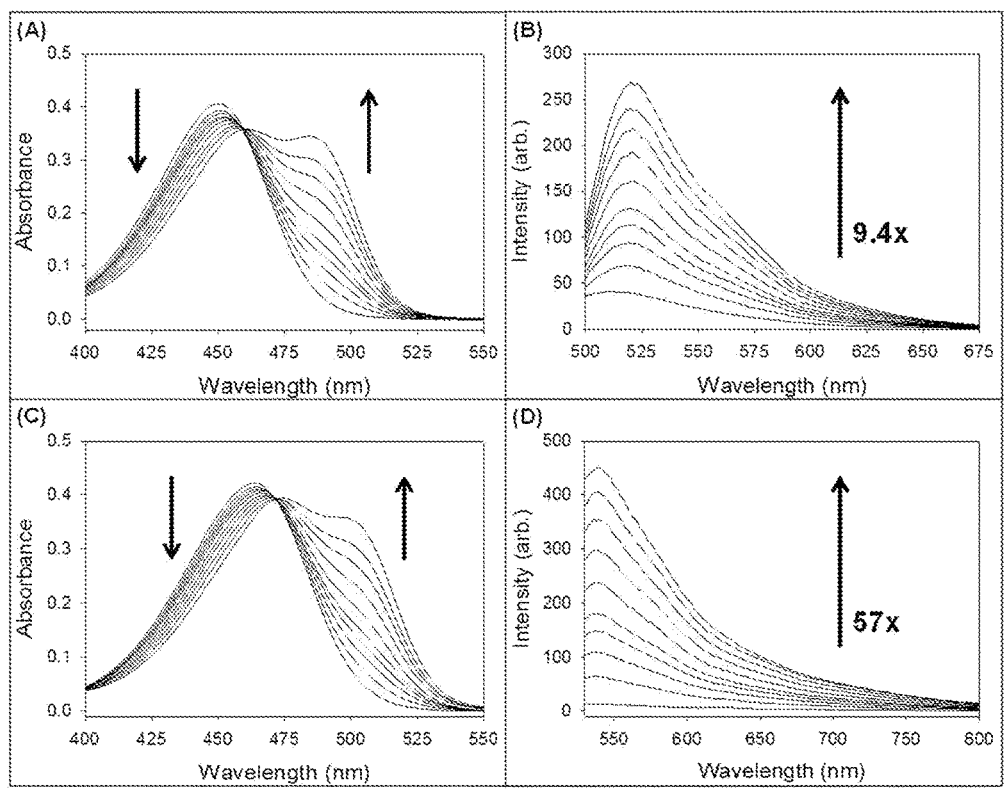
FIG. 14: (A) UV/Vis and (B) fluorescence titration of sensor 1b (10 μM) with aliquots of 500 mM glutamate in buffer (25 mM HEPES, 50 mM $Na_2S_2O_3$, pH=5.0, 37° C.). Excited at 488 nm. (C) UV/Vis and (D) fluorescence titration of sensor 2b (10 uM) with aliquots of 500 mM glutamate in buffer (25 mM HEPES, 50 mM $Na_2S_2O_3$, pH=5.0, 37° C.). Excited at 515 nm.

The sensors were titrated with glutamate as a representative amine and the absorption and fluorescence spectra recorded in buffer at pH 5 to mimic the acidic interior of the secretory vesicle. Representative spectral changes for sensors 1b and 2b upon binding with analyte are shown in FIG. 14. As observed with other sensors in this series, interaction with a primary amine produces a red shift in absorption. For the series 1 sensors, the absorption of the bound species shifted from approximately 448 nm to 488 nm. Similarly, the emission maxima of the series 1 sensors were red-shifted to approximately 520 nm upon binding, giving these sensors spectroscopic properties that conveniently match that of fluorescein. For the series 2 sensors, the absorbance shifts from approximately 467 nm to 502 nm upon interaction with glutamate and the emission shifts from approximately 522 to 540 nm, which is 20 nm longer in wavelength than the absorbance values for the series 1 sensors. The absorbance maxima, fluorescence emission, and fluorescence quantum yield ($\Phi_{fl}$) of the unbound and bound sensors were measured in buffer at pH 5.0 and tabulated in Tables 3 and 4 (set forth in FIGS. 20 and 21, respectively) along with the $E_{HOMO}$ and $E_{LUMO}$ values calculated using standard methods.

(c) Binding Affinities

The association constants ($K_a$) of each sensor toward glutamate, norepinephrine and dopamine are listed in Tables 5 and 6 for series 1 and 2, respectively (see Figures. The interaction between coumarin aldehydes and primary amines is a covalent reaction and, in principle, would be best represented as an equilibrium constant ($K_{eq}$). However, because most supramolecular interactions are measured in terms of association constant, that convention was adopted herein for the sake of comparison and ease of use. Tables 5 and 6 also list maximum fluorescent enhancements ($I_{sat}/I_0$), which are the fluorescence intensities at saturation (as determined by the fit to a one-site binding isotherm) relative to the fluorescence intensities of the unbound sensors. These data give the maximum possible fluorescence response and are useful in comparing the spectroscopic properties of the fully bound sensor to the unbound state as well as to other sensors.

(2) Discussion (a) Binding Affinity and Selectivity

Glutamate binds to all derivatives with the same relatively low affinity (5-10 M$^{-1}$). This result is consistent with other coumarin aldehyde sensors, which appear to bind all primary alkyl amines with similar low affinity. Surprisingly, the catecholamines bind roughly an order of magnitude better. Moreover, there is a clear trend toward better binding to sensors with more electron-rich aromatic groups in the C4-position. There appears to be subtle contact between the catechol group and the C4-aromatic, which increases with electron density on the C4-aromatic residue. Interestingly, the thiophene-based sensors demonstrated slightly lower overall affinity than the benzene-based sensors and the electronic structure of the thiophene does not appear to influence the binding constant of catecholamines. Although these binding constants are modest, they should suffice for cell imaging purposes because catecholamines are present at high concentrations (0.5-1 M) in secretory vesicles compared to the concentrations of typical amines present in a cell (5 mM) and would promote binding. Indeed, even glutamate is thought to be present in concentrations as high as 300 mM in vesicles of glutamatergic neurons. Given that NS521 appears to accumulate in vesicles (vide supra), it is possible that some of the sensors described here could be used to image glutamate as well as catecholamines.

(b) Spectroscopic Properties

Upon analyte addition, the fluorescence enhancements for the series 1 sensors were very good: as high as an 11-fold increase for glutamate and a 6.6-fold increase for norepinephrine. As the absorbance maximum shifts to the red upon interaction with the analyte, selective excitation of the red wavelength produces a fluorescence increase upon binding. In addition, the fluorescence quantum yields of the bound sensors were higher than those for the unbound sensors. Thus, the observed fluorescence enhancements are due to the selective excitation wavelength used and an increase in fluorescence quantum yield upon binding. Indeed, better enhancements might be possible by judicious choice of excitation wavelength; however, a wavelength of 488 nm was selected because it is commonly available for imaging applications. The catecholamines can quench by PET, which is reflected in a lower fluorescence quantum yield for the dopamine- and norepinephrine-bound sensors compared to sensors bound to glutamate. However, useful enhancements are seen even for those quenching analytes (Tables 5 and 6). It should be noted that sensors 1a and 1e required a DMSO cosolvent due to solubility issues, so the spectroscopic properties of these two sensors are not directly comparable to the others in this series.

The fluorescence response of the series 2 sensors to the primary amine analytes was markedly higher than the fluorescence response of the series 1 sensors: as high as 57-fold for glutamate and 48-fold for norepinephrine. The difference in fluorescence response can be attributed to a lower initial fluorescence baseline. From Table 4 (FIG. 21), the quantum yields of the unbound thiophene derivatives are lower than those for the unbound benzene derivatives; however, the change in quantum yield between bound and unbound state were similar to the series 1 sensors. The major difference in the case of the series 2 sensors is that they were excited at 515 nm to mimic a common laser line rather than exciting at the absorption maxima (~502 nm). At this higher excitation wavelength, the unbound derivative hardly absorbs, resulting in an overall low background that contributes to the very high fluorescence enhancements seen in Table 6 (FIG. 23).

(c) PET Influences on the Series 1 Sensors

Figure 12:
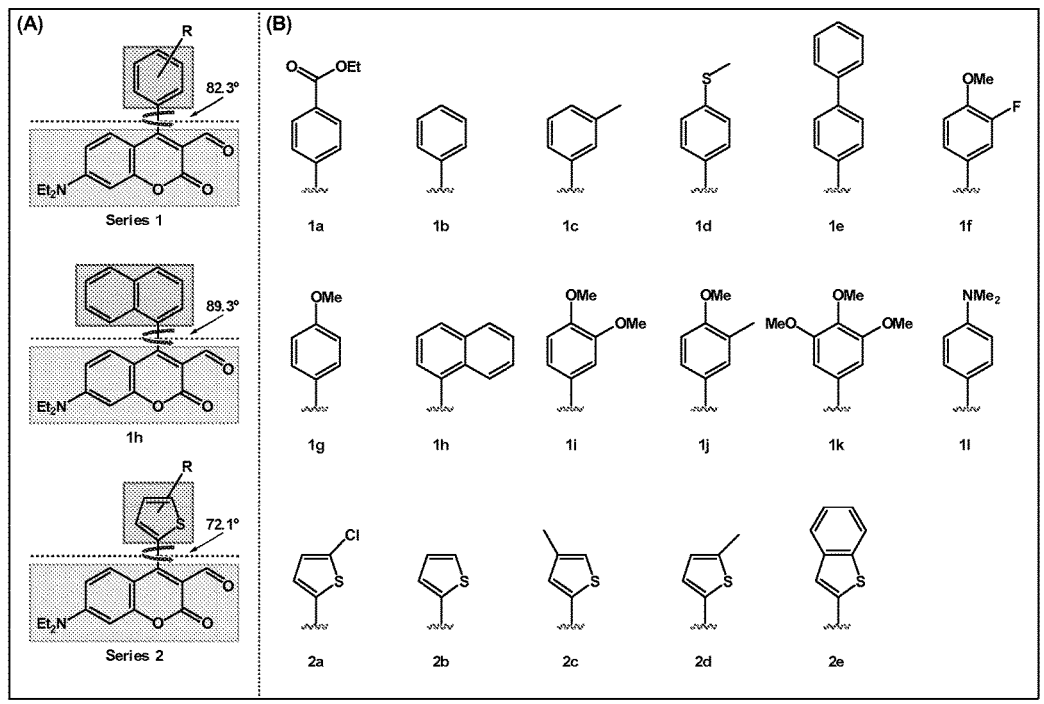
FIG. 12: (A) The sensor platform consists of a pendant aryl moiety (medium dark gray) directly linked to the C4-position of the coumarin-3-aldehyde scaffold (light gray). (B) Structures of derivatives used in this study: benzene-substituted series (1a-1) and thiophene-substituted series (2a-e).
Figure 15:
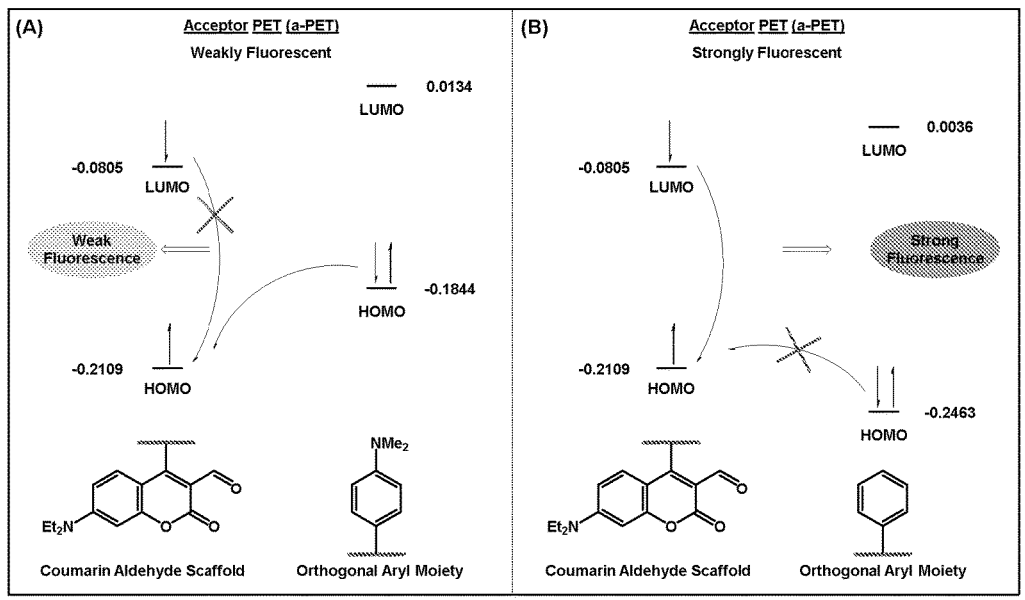
FIG. 15: Frontier orbital energy diagram of the PET process. (A) a-PET results in weak fluorescence. (B) Loss of a-PET quenching results in strong fluorescence.

Optimized models of the benzene-based sensors clearly indicate that the pendant aryl moiety is nearly perpendicular to the plane of the coumarin aldehyde scaffold (FIG. 12). The modeling results are supported by the fact that all of the benzene-based sensors (except 1h) have approximately the same absorbance and emission maxima, indicating that the ground-state interaction between the pendant aryl moiety and the coumarin aldehyde scaffold was similar in all of them. The $E_{HOMO}$ and $E_{LUMO}$ values of the coumarin aldehyde scaffold were calculated to be −0.2109 and −0.0805 hartrees, respectively (FIG. 15). The calculated $E_{LUMO}$ values of the pendant aryl moiety of the benzene-based sensors (summarized in Table 3 as set forth in FIG. 20) are significantly higher than the calculated $E_{LUMO}$ values of the coumarin aldehyde fluorophore, indicating that a d-PET process is not operative. In contrast, the calculated $E_{HOMO}$ values of the pendant aryl moiety are in the same range as the calculated $E_{HOMO}$ value of the coumarin aldehyde fluorophore, suggesting an a-PET mechanism can modulate the fluorescence properties of the coumarin. Thus, the C4-aryl moiety can be used to control the fluorescence properties of the coumarin aldehyde fluorophore.

This analysis also explains the differential fluorescence response of the sensors to the various analytes (Table 7, FIG. 24). In all cases, dopamine and norepinephrine produce a lower fluorescence response than glutamate does. The calculated $E_{HOMO}$ values of the catecholamines (Table 7, FIG. 24) indicate that these analytes should act as PET quenchers, with dopamine being a better PET quencher than norepinephrine. Indeed, this expectation was borne out from the observed fluorescence enhancements. Further, the calculated $E_{HOMO}$ value of serotonin is significantly higher than the $E_{HOMO}$ values for both catecholamines, indicating that serotonin should be a considerably better PET quencher of the coumarin aldehyde fluorophore. Indeed, serotonin completely quenches the fluorescence response of all sensor derivatives upon binding (data not shown).

(d) Quantitative Study of the PET Process in Series 1 Sensors

As can be seen in Table 3 (FIG. 20), a wide range of fluorescence quantum yields was observed with the more electron rich pendant aryl moieties giving much stronger quenching. Interestingly, the quantum yields of the bound species are uniformly higher than the unbound species. The iminium ion formed upon binding has a lower calculated $E_{HOMO}$ value (−0.3373 hartrees) than the aldehyde (−0.2109 hartrees) and thus, would be subject to stronger quenching by the C4-aromatic group. However, this quenching effect is more than offset by the formation of the iminium ion which stabilizes and rigidifies the ITC state resulting in an overall increase in quantum yield upon binding.

Figure 16:
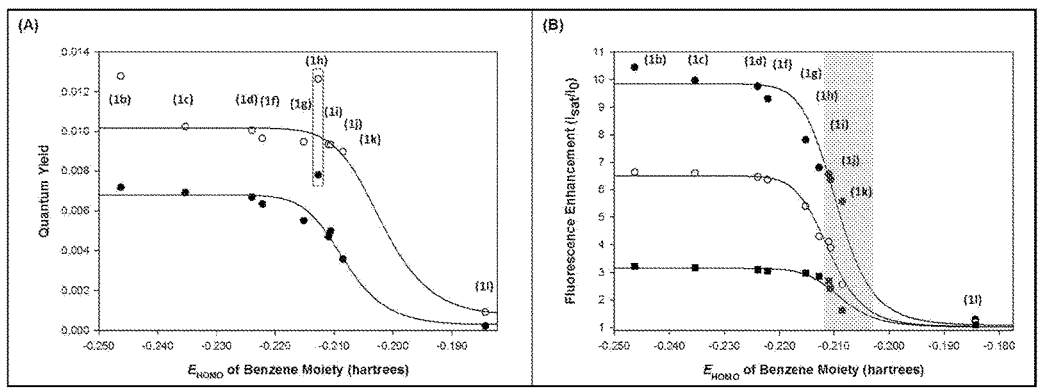
FIG. 16: (A) Relationship between the calculated $E_{HOMO}$ values of the pendant aryl moiety and the fluorescence quantum yields for series 1 sensors (●) unbound and (○) bound with glutamate. The gray box outline highlights naphthalene derivative. (B) Relationship between the calculated $E_{HOMO}$ values of the pendant aryl moiety and the fluorescence enhancement for series 1 sensors with (●) glutamate, (○) norepinephrine, and (■) dopamine. The shaded region identifies derivatives with selective fluorescent responses. The curves represent the best fit to the Marcus equation.

To evaluate the photophysical interaction between the pendant aryl moiety and the coumarin aldehyde scaffold, the relationship between the quantum yield for the unbound and bound series 1 sensors and the calculated $E_{HOMO}$ values of the corresponding benzene moiety was plotted and fit to the Marcus equation on the basis of the calculated $E_{HOMO}$ values (FIG. 16). The calculated free energy change for electron transfer ($\Delta G_{ET}$) values, a prerequisite for fluorescence analysis in terms of Marcus theory, were obtained as per the Rehm-Weller equation. The calculated free energy change for electron transfer ($\Delta G_{ET}$) values were derived, in part, from the oxidation and reduction potential values using an established linear correlation between the molecular orbital energy values ($E_{HOMO}$ and $E_{LUMO}$) and the experimentally measured oxidation and reduction potential values. The experimentally determined quantum yields aligned with the fitted curves quite well, indicating that the sensor platform fits the model of a directly linked donor-acceptor system. In the case of compound 1h having the 1-naphthyl group, both the unbound and bound quantum yields of 1h are higher than theory would predict. However, this difference is attributed to the greater rigidification of the fluorophore (vide infra) because the C4-naphthyl moiety is closer to 90° from the plane of the fluorophore (FIG. 12).

Because the absorbance maxima of the series 1 sensors were similar in both unbound and bound forms, the differences in fluorescent enhancement ($I_{sat}/I_0$) from Table 5 (FIG. 22) are due entirely to variations in quantum yield between the two forms. Thus, these maximum fluorescence changes were plotted versus the calculated $E_{HOMO}$ values (FIG. 16B) and the same trends were observed as when plotting just the quantum yield. Indeed, compound 1h, which was an outlier in FIG. 16A, falls in line with the other derivatives in such a plot, indicating that the effect of the naphthyl group on the quantum yield was similar in both the bound and unbound states. Interestingly, the fluorescence enhancement for the series 1 sensors toward glutamate, norepinephrine, and dopamine followed a similar relationship, indicating that quenching analytes such as dopamine can quench all the sensors to the same degree. From this type of analysis, it is possible to identify sensors that would give selective turn-on fluorescent responses. For example, compounds in the gray region of FIG. 16B should give a good response to glutamate, but much weaker response to dopamine and norepinephrine. Of the sensors tested here, compound 1k appears to be the best glutamate-selective sensor. Taken together, these results support the notion that an a-PET process modulates the fluorescence properties of the sensor platform and establishes a method for the rational design of selective sensors for primary amine neurotransmitters by variation of the C4-substituent.

(e) Variation in the Quantum Yields for the Series 2 Sensors

Figure 17:
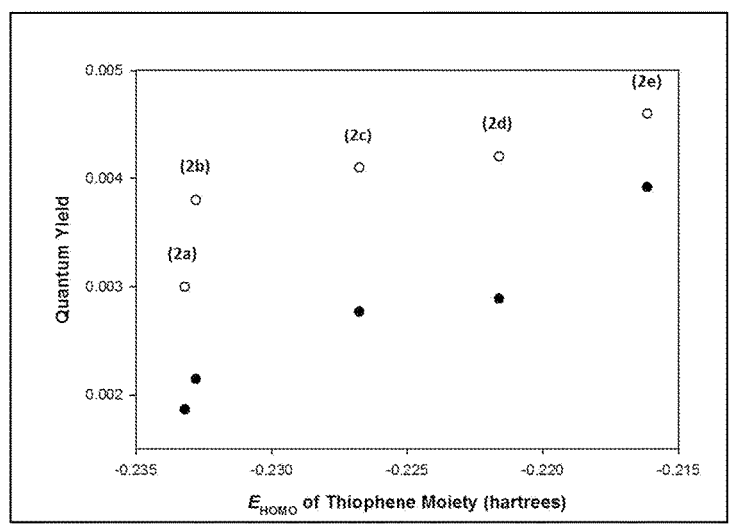
FIG. 17: Relationship between the calculated $E_{HOMO}$ values of the pendant aryl moiety and the fluorescence quantum yields for series 2 sensors (●) unbound and (○) bound with glutamate.

Calculations indicated that the thiophene substituents have more π-overlap with the fluorophore than the phenyl groups of the series 1 sensors. This overlap causes the absorbance and emission of the series 2 sensors to be at longer wavelengths. Indeed, the trends indicated that the more electron-rich thiophenes display higher wavelengths of excitation and emission. However, the quantum yields of the thiophene derivatives were lower than that of most of the series 1 sensors. This low quantum yield effect has been observed in other directly linked donor-acceptor systems (platforms) and has sometimes been attributed to PET quenching from the thiophene. The calculated $E_{HOMO}$ and $E_{LUMO}$ values of the series 2 sensors (Table 4, FIG. 21) indicate that the a-PET mechanism is not operational in these derivatives. For the series 2 sensors, the quantum yields trend upward as the group becomes more electron rich (FIG. 17). It should be noted that for the chlorothiophene derivative (2a), it is possible that quenching due to the heavy atom effect of the chlorine may contribute to an anomalously low quantum yield for this sensor. Regardless, it is clear that PET quenching does not explain the low quantum yield of the thiophene derivatives.

If one compares the quantum yield of the naphthalene derivative (1h) to the other benzene derivatives (e.g., 1b) and the thiophene derivatives (e.g., 2b), the sensors in which the C4-group is more perpendicular and thereby, more rigid, have higher fluorescence quantum yields than those where the C4-group is more in plane with the coumarin aldehyde scaffold and thereby, less rigid (FIG. 12). These results indicate that twisting of the aryl-fluorophore bond in the excited state leads to non-radiative decay processes and lowers the quantum yield of the fluorophore.

(f) Summary of the Fluorescence Responses

Figure 18:
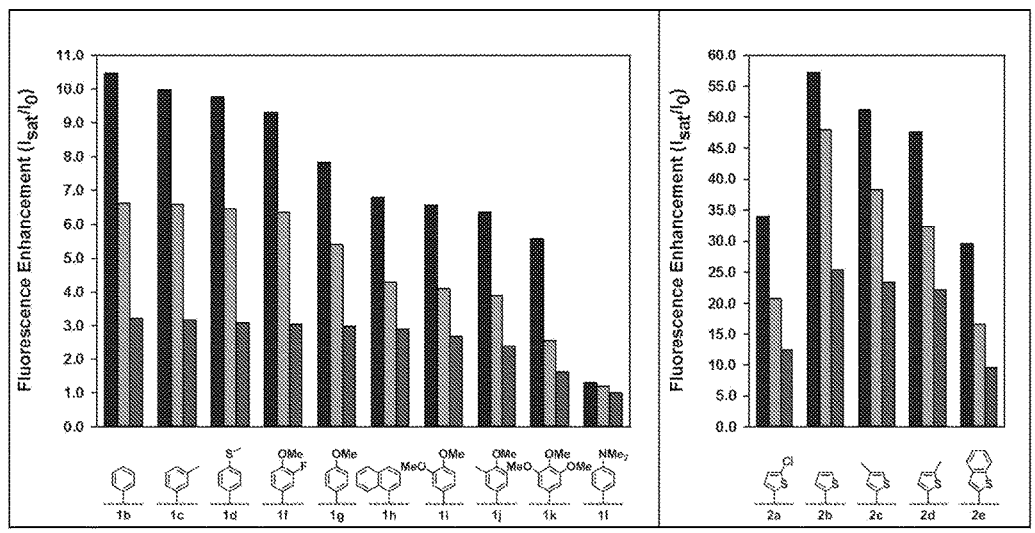
FIG. 18: The fluorescence enhancements of (A) series 1 and (B) series 2 derivatives toward glutamate (black ■), norepinephrine (light gray ▨), and dopamine (medium dark gray ▨).

The fluorescence enhancements for the series 1 and 2 sensors upon binding to glutamate, norepinephrine, and dopamine are summarized in FIG. 18. It should be noted that sensor 1g (NS521) does not have the highest fluorescence response of the series 1 sensors. However, sensor 1g was selected because it struck a good balance between high fluorescence responses and good binding affinity toward norepinephrine and dopamine that would provide selective labeling and imaging in cellular studies. Overall, compared to the benzene-based series 1 sensors, the thiophene-based series 2 sensors provided only subtle differences in binding constants. However, the fluorescence enhancements for the thiophene-based series were considerably larger than the fluorescence enhancements for the benzene-based series. Of this series, sensor 2b had the highest fluorescence enhancements due to a high ratio of quantum yields between the unbound and bound sensor as well as high binding affinities toward the primary-amine analytes. Given the high fluorescence enhancements and red-shifted fluorescence properties observed for compound 2b (Table 5, FIG. 22), this compound was named NeuroSensor 539 (NS539) and cell imaging studies were pursued.

(g) Confocal Fluorescence Spectroscopy

Figure 19:
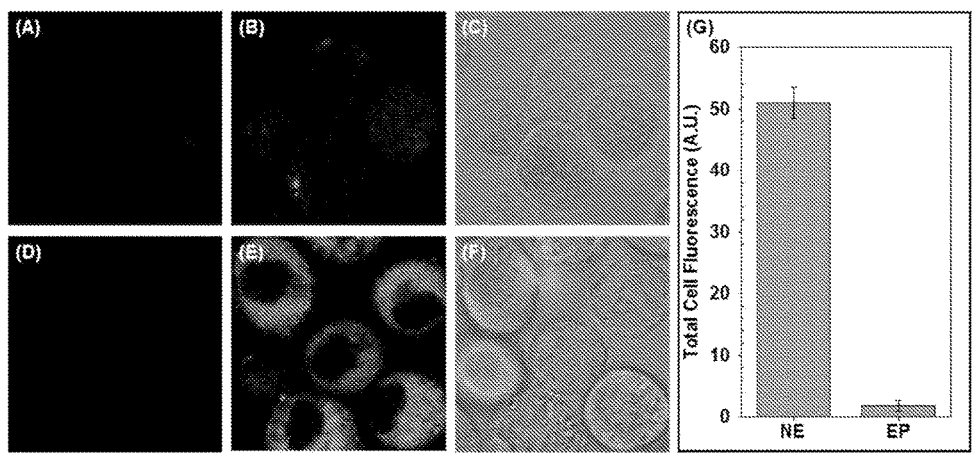
FIG. 19: Epinephrine-enriched cells (A-C) incubated with NS539 (2b, 10 μM): (A) $\lambda_{ex}$=458 nm; (B) $\lambda_{ex}$=514 nm; (C) brightfield image. Norepinephrine-enriched cells (D-F) incubated with NS539 (2b, 10 μM): (D) $\lambda_{ex}$=458 nm; (E) $\lambda_{ex}$=514 nm; (F) brightfield image. Fluorescence was visualized using a 535-590 nm bandpass filter. (G) The mean corrected total cell fluorescence intensity for norepinephrine- and epinephrine-enriched (NE and EP, respectively) cells was 51.0±2.6 and 1.86±0.98 respectively. Error bars represent standard deviation (n=6).

Norepinephrine- and epinephrine-secreting chromaffin cells were isolated from bovine adrenal glands, separately incubated with NS539 (2b, 10 μM), and imaged using confocal fluorescence microscopy. The live cells were imaged at 458 nm which would excite any potential unbound sensor and at 514 nm which would excite the bound sensor. Excitation of the epinephrine cells at 514 nm provided marginal fluorescence response, indicating that the sensor is not binding to epinephrine (FIG. 19B) as expected since epinephrine is a secondary-amine neurotransmitter (FIG. 11). Indeed, excitation at 458 nm gave no fluorescence, indicating that the unbound neutral sensor does not remain inside the cell (FIG. 19A). However, the norepinephrine-enriched cells exhibited strong punctate fluorescence upon excitation at 514 nm (FIG. 19E). Exciting the norepinephrine-enriched cells at the wavelength associated with the unbound sensor ($\lambda_{ex}$=458 nm) similarly provided no measurable fluorescence response (FIG. 19D). The results indicate that the NS539 only accumulates within secretory vesicles upon binding to norepinephrine, as previously seen with NS521. The ratio of the mean corrected total cell fluorescence intensity of norepinephrine- over epinephrine-enriched cells was approximately 27-fold (FIG. 19G). These results validate NS539 as an excellent sensor for cellular imaging of primary-amine neurotransmitters with very low background.

(3) Conclusion

These data suggest that the coumarin-3-aldehyde scaffold and pendant aryl-based moiety comprise a platform that constitutes a new directly linked donor-acceptor system when the pendant aryl moiety is benzene-based, and thus, perpendicular to the plane of the fluorophore. The benzene-substituted series of sensors operates via an a-PET mechanism, which allows one to predict both the fluorescence quantum yields and the fluorescence responses toward primary-amine neurotransmitters based on DFT calculations. The results provide a rational design strategy for the development of turn-on fluorescent sensors for primary-amine neurotransmitters based on the coumarin-3-aldehyde scaffold. The thiophene-substituted series of sensors did not follow the same trend based on PET quenching, indicating that the π-system of the thiophene is more conjugated with that of the fluorophore. However, due to favorable excitation/emission profiles, the thiophene sensors gave far superior fluorescence enhancements upon binding analytes. Based on these studies, NeuroSensor 539 was identified as a good candidate for biological imaging studies by demonstrating enhanced spectral and photophysical properties. The efficacy of NeuroSensor 539 was validated by selectively labeling and imaging norepinephrine in secretory vesicles of live chromaffin cells using longer excitation wavelengths that provided lower background.

(4) Experimental (a) Materials and General Instrumentation

All chemicals were obtained from Acros Organics, Sigma-Aldrich, Alfa Aesar, Combi-Blocks or Fisher Scientific and were used without further purification. Flash chromatography was performed with 32-63 μm silica gel. $^1$H NMR and $^{13}$C NMR spectra were recorded on a Bruker DRX 500. IR spectra were recorded on a Nexus 670 FT-IR E.S.P. spectrometer. Distilled water was used to prepare all aqueous solutions.

(b) Computational Methods

Conventional DFT calculations using the hybrid exchange-correlation function B3LYP with the 6-31G(d) basis set as implemented in Gaussian 09W were performed on the benzene- and thiophene-based coumarin-3-aldehyde derivatives. Several starting geometries were used for the geometry optimization to ensure that the optimized structure corresponds to a global minimum.

(c) Fluorescence Titrations

Fluorescence spectra were recorded on a Shimadzu RF-5301 PC spectrofluorometer at 37° C. A separate 1 mg/mL stock solution of each coumarin-3-aldehyde derivative in DMSO was prepared. An aqueous stock solution of each derivative (10 μM) in buffer (25 mM HEPES, 50 mM $Na_2S_2O_3$, pH=5.0) was prepared. Norepinephrine, dopamine, glutamate, and epinephrine stock solutions were prepared by separately dissolving the solid analytes at the concentration to be used in the titration with the buffered stock solutions described above and thus, avoiding dilution of the sensor during the experiment. The benzene-based NS521 derivatives were excited at 488 nm. The thiophene-based derivatives were excited at 515 nm.

(d) Fluorescence Properties and Quantum Yields

Steady-state fluorescence spectroscopic studies were performed using a Horiba Scientific Fluorolog-3 Model FL3C-111 spectrofluorometer and data was collected and analyzed using HJY FluorEssence™ 3.5.1.20 software package. UV-visible spectra were obtained on a Varian Cary 1E UV-visible spectrophotometer. A stock solution of each benzene- or thiophene-based coumarin-3-aldehyde derivative (1 μM) in buffer (25 mM HEPES, 50 mM $Na_2S_2O_3$, pH=5.0) was prepared. Each solution contained 1% (v/v) DMSO as a cosolvent except as noted. The slit width was 2 nm for both excitation and emission. The bound benzene- and thiophene-coumarin-3-aldehyde derivatives contained 500 mM glutamate (pH=5.0).

To determine the relative quantum yield of fluorescence ($\Phi_{fl}$) for the benzene-based derivatives, a 1.0 μM solution of fluorescein (absolute $\Phi_{fl}$=0.85) in 0.1 N NaOH (pH 13) was used as a fluorescence standard. The unbound derivatives were excited at 473 nm and the bound derivatives were excited at 488 nm. To determine the relative quantum yield of fluorescence ($\Phi_{fl}$) for the thiophene-based derivatives, a 1.0 μM solution of rhodamine B (absolute $\Phi_{fl}$=0.31) in water (pH 7) was used as a fluorescence standard. The unbound derivatives were excited at 473 nm and the bound derivatives were excited at 515 nm. Quantum yields were obtained in triplicate and calculated as per the following equation:

$$\Phi_S = \Phi_R \times \frac{I_S}{I_R} \times \frac{A_R}{A_S} \times \frac{n_S^2}{n_R^2}$$

where $\Phi_S$=relative quantum yield of the sample, $\Phi_S$=absolute quantum yield of the reference, $I_S$=integrated fluorescence intensity of the sample, $I_R$=integrated fluorescence intensity of the reference, $A_R$=absorbance of the reference, $A_S$=absorbance of the sample, $n_S$=refractive index of the sample solvent, and $n_R$=refractive index of the reference solvent.

(e) Fluorescence Imaging in Live Cells

Chromaffin cells were prepared as previously described. Approximately 3 mL of each culture media containing suspended epinephrine- and norepinephrine-enriched cells was centrifuged at 1,000 rpm for 5 min. The pellets were suspended in 2 mL Dulbecco's Modified Eagle Medium (DMEM). NS539 was added (10 µM final concentration) and each cell suspension containing sensor incubated at 37° C. for 30 min. The cells were centrifuged, the supernatant removed, and washed twice with PBS buffer. Next, the cells were taken up into 6 mL standard cell bath solution and plated onto No. 1.5 γ-irradiated poly-D-lysine coated 35 mm glass-bottom dishes (MatTek Corporation). The cells incubated on the dishes 37° C. with 5% $CO_2$ for 1 hr prior to imaging to promote adhesion. Live cell imaging studies were performed using a Zeiss LSM 510 META laser scanning confocal microscope (Carl Zeiss Microscopy, LLC) equipped with a C-Apochromat 63x/1.2 water immersion objective lens (Carl Zeiss Microscopy, LLC). The excitation wavelengths were 458 nm and 514 nm (pixel time: 6.4 µs, detector gain: 845, amplifier gain: 1.00, amplifier offset: −0.05, pinhole: 328 µm). Image acquisition was performed using Zeiss AIM 4.2 software package (Carl Zeiss Microscopy, LLC). To compare the fluorescence intensities of the norepinephrine- vs. the epinephrine-enriched cells, the mean corrected total cell fluorescence intensities were obtained using ImageJ (National Institute of Health).

(f) General Procedure for Synthesis of Sensors 1a-1 and 2e

Compound 3 (0.250 g, 0.894 mmol), arylboronic acid 4a-1 or 6e (0.983 mmol), bis(dibenzylideneacetone)-palladium(0) (0.041 g, 0.045 mmol), 2-dicyclohexylphosphino-2′,6′-dimethoxybiphenyl (SPhos) (0.055 g, 0.134 mmol), tribasic potassium phosphate (0.381 g, 1.788 mmol) were added to a flame-dried round bottom flask and flushed with $N_2$ for 30 minutes. Degassed THF (distilled, 6 mL) was added and the mixture stirred at 60° C. for 12-24 hours under $N_2$. The mixture was allowed to cool to room temperature, filtered through paper, rinsed with acetone, and the solvent removed in vacuo. The crude residue was purified by silica gel flash chromatography (100% $CH_2Cl_2$→80:20 $CH_2Cl_2$/EtOAc as eluent). The material was further purified by silica gel flash chromatography (90:10 hexanes/EtOAc→50:50 hexanes/EtOAc as eluent) to afford compounds 1a-1 and 2e as yellow oils.

(i) Data for Compound 1a

Yield: 83%. $^1$H NMR (500 MHz, $CDCl_3$) δ 9.95 (s, 1H), 8.18 (d, 2H, J=8.0 Hz), 7.32 (d, 2H, J=8.5 Hz), 6.84 (d, 1H, J=9.0 Hz), 6.52 (d, 1H, J=2.5 Hz), 6.49 (dd, 1H, J=9.0, 2.5 Hz), 4.43 (q, 2H, J=7.0 Hz), 3.45 (q, 4H, J=7.5 Hz), 1.43 (t, 3H, J=7.0 Hz), 1.23 (t, 6H, J=7.0 Hz); $^{13}$C NMR (125 MHz, $CDCl_3$) δ 188.0, 166.0, 160.5, 159.7, 157.8, 153.1, 138.3, 130.9, 130.8, 129.6, 128.1, 111.7, 109.9, 108.8, 97.1, 61.2, 45.2, 14.3, 12.4; IR (neat, $cm^{-1}$) 2978, 1716, 1614, 1556, 1499, 1356, 1270, 1127, 1103, 727; HRMS calculated for $C_{23}H_{23}NO_5Na$ (M+Na$^+$): 416.1468. Found: 416.1464.

(ii) Data for Compound 1b

Yield: 64%. $^1$H NMR (500 MHz, $CD_2Cl_2$) δ 9.78 (s, 1H), 7.47-7.55 (m, 3H), 7.23-7.30 (m, 2H), 6.93 (d, 1H, J=10.0 Hz), 6.50-6.57 (m, 2H), 3.45 (q, 4H, J=7.0 Hz), 1.23 (t, 6H, J=7.0 Hz); $^{13}$C NMR (125 MHz, $CD_2Cl_2$) δ 188.4, 162.0, 159.9, 158.1, 153.4, 133.7, 131.2, 129.3, 128.8, 128.7, 112.7, 110.2, 109.5, 97.4, 45.6, 12.5; IR (neat, $cm^{-1}$) 2974, 1751, 1715, 1683, 1617, 1559, 1504, 1418, 1354; HRMS calculated for $C_{20}H_{19}NO_3Na$ (M+Na$^+$): 344.1257. Found: 344.1254.

(iii) Data for Compound 1c

Yield: 82%. $^1$H NMR (500 MHz, $CDCl_3$) δ 9.79 (s, 1H), 7.39 (t, 1H, J=8.0 Hz), 7.31 (d, 1H, J=8.0 Hz), 7.06-7.09 (m, 2H), 6.98 (d, 1H, J=10.0 Hz), 6.48-6.53 (m, 2H), 3.43 (q, 4H, J=7.0 Hz), 2.42 (s, 3H), 1.22 (t, 6H, J=7.0 Hz); $^{13}$C NMR (125 MHz, $CDCl_3$) δ 188.4, 162.6, 159.4, 157.7, 153.0, 138.2, 132.8, 131.0, 129.9, 129.0, 128.3, 125.6, 112.3, 109.6, 109.0, 97.0, 45.1, 21.4, 12.4; IR (neat, $cm^{-1}$) 1744, 1712, 1614, 1556, 1503, 1417, 1352, 1127, 730; HRMS calculated for $C_{21}H_{21}NO_3Na$ (M+Na$^+$): 358.1414. Found: 358.1413.

(iv) Data for Compound 1d

Yield: 36%. $^1$H NMR (500 MHz, $CDCl_3$) δ 9.88 (s, 1H), 7.36 (d, 2H, J=8.5 Hz), 7.20 (d, 2H, J=8.5 Hz), 7.01 (d, 1H, J=8.0 Hz), 6.48-6.52 (m, 2H), 3.45 (q, 4H, J=7.0 Hz), 2.56 (s, 3H), 1.24 (t, 6H, J=7.0); $^{13}$C NMR (125 MHz, $CDCl_3$) δ 188.3, 161.3, 159.9, 157.8, 153.0, 140.5, 130.9, 129.3, 129.0, 125.7, 112.3, 109.6, 109.0, 97.1, 45.2, 15.3, 12.4; IR (neat, $cm^{-1}$) 1746, 1714, 1612, 1558, 1507, 1487, 1420, 1353, 1132; HRMS calculated for $C_{21}H_{21}NO_3SNa$ (M+Na$^+$): 390.1134. Found: 390.1132.

(v) Data for Compound 1e

Yield: 25%. $^1$H NMR (500 MHz, $CDCl_3$) δ 9.92 (s, 1H), 7.74 (d, 2H, J=8.5 Hz), 7.68 (d, 2H, J=8.0 Hz), 7.50 (t, 2H, J=7.5 Hz), 7.42 (t, 1H, J=7.5 Hz), 7.36 (d, 2H, J=8.0 Hz), 7.06 (d, 1H, J=9.5 Hz), 6.51-6.56 (m, 2H), 3.45 (q, 4H, J=7.5 Hz), 1.26 (t, 6H, J=7.5 Hz); $^{13}$C NMR (125 MHz, $CDCl_3$) δ 188.4, 161.7, 159.8, 157.8, 153.1, 142.0, 140.1, 131.9, 131.0, 129.0, 128.9, 127.8, 127.2, 127.1, 112.4, 109.7, 109.1, 97.1, 45.2, 12.4; IR (neat, $cm^{-1}$) 1745, 1711, 1610, 1558, 1498, 1419, 1352, 1131; HRMS calculated for $C_{26}H_{23}NO_3Na$ (M+Na$^+$): 420.1570. Found: 420.1568.

(vi) Data for Compound 1f

Yield: 69%. $^1$H NMR (500 MHz, $CDCl_3$) δ 9.91 (s, 1H), 7.09 (t, 1H, J=8.5 Hz), 6.98-7.03 (m, 3H), 6.49-6.55 (m, 2H), 3.98 (s, 3H), 3.46 (q, 4H, J=7.0 Hz), 1.22 (t, 6H, J=7.0 Hz); $^{13}$C NMR (125 MHz, $CDCl_3$) δ 188.2, 160.1, 159.8, 157.8, 153.0, 152.9, 151.0, 148.4, 148.3, 130.8, 125.5, 125.4, 124.8, 116.6 (C-F, d, J=20.0 Hz), 113.2, 113.1, 112.2, 109.8, 109.0, 97.1, 56.3, 45.2, 12.4; IR (neat, $cm^{-1}$) 1747, 1614, 1556, 1520, 1499, 1429, 1417, 1354, 1270, 1136; HRMS calculated for $C_{21}H_{20}FNO_4Na$ (M+Na$^+$): 392.1268. Found: 392.1267.

(vii) Data for Compound 1h

Yield: 67%. $^1$H NMR (500 MHz, $CDCl_3$) δ 9.72 (s, 1H), 7.98 (d, 1H, J=8.5 Hz), 7.94 (dd, 1H, J=8.5, 1.5 Hz), 7.58 (t, 1H, J=7.5 Hz), 7.48-7.54 (m, 2H), 7.41 (td, 1H, J=8.0, 1.0 Hz), 7.34 (dd, 1H, J=7.0, 1.0 Hz), 6.70 (d, 1H, J=9.0), 6.55 (d, 1H, J=2.5 Hz), 6.37 (dd, 1H, J=9.5, 2.5 Hz), 3.42 (q, 4H, J=7.0 Hz), 1.21 (t, 6H, J=7.0 Hz); $^{13}$C NMR (125 MHz, $CDCl_3$) δ 188.0, 161.1, 159.7, 153.2, 133.2, 131.1, 131.0, 130.9, 129.3, 128.5, 127.1, 126.5, 126.0, 125.1, 125.0, 113.3, 109.8, 109.5, 96.9, 45.2, 12.4; IR (neat, $cm^{-1}$) 1744, 1716, 1679, 1614, 1552, 1499, 1417, 1352, 1136; HRMS calculated for $C_{24}H_{21}NO_3Na$ (M+Na$^+$): 394.1414. Found: 394.1413.

(viii) Data for Compound 1i

Yield: 77%. $^1$H NMR (500 MHz, $CDCl_3$) δ 9.82 (s, 1H), 7.08 (d, 1H, J=9.0 Hz), 7.00 (d, 1H, J=8.0 Hz), 6.87 (dd, 1H, J=8.0, 2.0 Hz), 6.80 (d, 1H, J=1.5 Hz), 6.50-6.55 (m, 2H), 3.97 (s, 3H), 3.88 (s, 3H), 3.46 (q, 4H, J=7.0 Hz), 1.25 (t, 6H, J=7.0 Hz); $^{13}$C NMR (125 MHz, $CDCl_3$) δ 188.5, 162.2, 159.4, 157.7, 153.0, 149.8, 148.9, 130.9, 125.0, 121.6, 112.6, 111.9, 110.9, 109.6, 109.1, 97.1, 56.1, 56.0, 45.2, 12.4; IR (neat, cm$^{-1}$) 2974, 1736, 1650, 1615, 1506, 1455, 1377, 1168; HRMS calculated for $C_{22}H_{23}NO_5Na$ (M+Na$^+$): 404.1468. Found: 404.1465.

(ix) Data for Compound 1j

Yield: 54%. $^1$H NMR (500 MHz, CDCl$_3$) δ 9.75 (s, 1H), 7.03-7.10 (m, 3H), 6.91 (d, 1H, J=8.5 Hz), 6.50 (dd, 1H, J=8.5, 2.0 Hz), 6.48 (d, 1H, J=2.0 Hz), 3.89 (s, 3H), 3.43 (q, 4H, J=7.0 Hz), 2.25 (s, 3H), 1.21 (t, 6H, J=7.0 Hz); $^{13}$C NMR (125 MHz, CDCl$_3$) δ 188.6, 162.8, 159.2, 158.6, 157.6, 152.9, 131.1, 130.9, 127.8, 126.8, 124.0, 112.5, 109.5, 109.4, 109.0, 96.9, 55.4, 45.1, 16.2, 12.4; IR (neat, cm$^{-1}$) 1746, 1611, 1511, 1495, 1419, 1353, 1251, 1137; HRMS calculated for $C_{22}H_{23}NO_4Na$ (M+Na$^+$): 388.1519. Found: 388.1518.

(x) Data for Compound 1k

Yield: 37%. $^1$H NMR (500 MHz, CDCl$_3$) δ 9.81 (s, 1H), 7.08 (d, 1H, J=9.0 Hz), 6.55 (dd, 1H, J=9.0, 2.5 Hz), 6.52 (d, 1H, J=2.5 Hz), 6.51 (s, 2H), 3.94 (s, 3H), 3.86 (s, 6H), 3.46 (q, 4H, J=7.0 Hz), 1.24 (t, 6H, J=7.0 Hz); $^{13}$C NMR (125 MHz, CDCl$_3$) δ 188.3, 162.3, 159.1, 157.7, 153.4, 138.5, 130.8, 128.2, 112.4, 109.7, 108.8, 105.9, 97.0, 61.1, 56.3, 45.2, 12.4; IR (neat, cm$^{-1}$) 1748, 1618, 1495, 1417, 1352, 1123; HRMS calculated for $C_{23}H_{25}NO_6Na$ (M+Na$^+$): 434.1574. Found: 434.1570.

(xi) Data for Compound 1l

Yield: 10%. $^1$H NMR (500 MHz, CDCl$_3$) δ 9.77 (s, 1H), 7.24 (d, 1H, J=8.0 Hz), 7.21 (d, 2H, J=7.0 Hz), 6.79 (d, 2H, J=9.0 Hz), 6.49-6.54 (m, 2H), 3.45 (q, 4H, J=7.0 Hz), 3.07 (s, 6H), 1.23 (t, 6H, J=7.0 Hz); $^{13}$C NMR (125 MHz, CDCl$_3$) δ 199.9, 163.4, 159.3, 157.7, 152.7, 151.2, 131.0, 130.9, 119.1, 112.5, 111.3, 109.3, 109.1, 97.1, 45.1, 40.2, 12.5; IR (neat, cm$^{-1}$) 1743, 1610, 1558, 1496, 1418, 1355, 1132; HRMS calculated for $C_{22}H_{24}N_2O_3Na$ (M+Na$^+$): 365.1860. Found: 365.1860.

(xii) Data for Compound 2e

Yield: 89%. $^1$H NMR (500 MHz, CDCl$_3$) δ 9.99 (s, 1H), 7.88 (dd, 1H, J=8.5, 1.5 Hz), 7.85 (dd, 1H, J=7.0, 2.0 Hz), 7.40-7.48 (m, 2H), 7.35 (s, 1H), 7.29 (d, 1H, J=9.0 Hz), 6.50-6.56 (m, 2H), 3.46 (q, 4H, J=7.0 Hz), 1.24 (t, 6H, J=7.0 Hz); $^{13}$C NMR (125 MHz, CDCl$_3$) δ 187.7, 159.2, 157.5, 154.3, 153.2, 140.7, 139.2, 132.9, 130.7, 126.1, 125.3, 125.0, 124.2, 122.2, 113.2, 109.9, 109.0, 97.0, 45.2, 12.4; IR (neat, cm$^{-1}$) 1742, 1615, 1491, 1418, 1356, 1268, 1148, 723; HRMS calculated for $C_{22}H_{19}NO_3SNa$ (M+Na$^+$): 400.0978. Found: 400.0977.

(g) General Procedure for Synthesis of Precursors 7a-d

Compound 5 (250.0 mg, 1.072 mmol), p-toluenesulfonyl chloride (224.8 mg, 1.179 mmol), and Na$_2$CO$_3$ (340.8 mg, 3.215 mmol) were added to a flame-dried round bottom flask and flushed with N$_2$ for 15 minutes. Degassed H$_2$O/THF (1:20, 15.0 mL) was added and the mixture stirred at 50° C. for 30 minutes. The mixture was allowed to cool to room temperature. Thiophene-based boronic acid 6a-d (1.179 mmol) was added to the mixture and was allowed to stir at room temperature for 5 minutes. Palladium chloride (9.5 mg, 0.054 mmol) was added and the mixture stirred at 50° C. for 6 hours. The mixture was filtered through paper and the solvent removed in vacuo. The remaining residue was purified by chromatography (100% CH$_2$Cl$_2$→95:5 CH$_2$Cl$_2$/EtOAc as eluent). The material was further purified by chromatography (90:10 hexanes/EtOAc→50:50 hexanes/EtOAc as eluent) to afford the compounds 7a-d as pale yellow oils.

(i) Data for Compound 7a

Yield: 26%. $^1$H NMR (500 MHz, CDCl$_3$) δ 7.64 (d, 1H, J=9.0 Hz), 7.16 (d, 1H, J=4.0 Hz), 7.01 (d, 1H, J=4.0 Hz), 6.58 (dd, 1H, J=9.0, 2.5 Hz), 6.55 (d, 1H, J=2.5 Hz), 6.07 (s, 1H), 3.43 (q, 4H, J=7.0 Hz), 1.22 (t, 6H, J=7.0 Hz); $^{13}$C NMR (125 MHz, CDCl$_3$) δ 161.6, 156.8, 150.8, 147.1, 135.6, 132.6, 128.0, 127.2, 126.9, 108.7, 108.1, 106.7, 98.0, 44.8, 12.4; IR (neat, cm$^{-1}$) 2974, 1712, 1614, 1585, 1516, 1434, 1352, 1266, 1103; HRMS calculated for $C_{17}H_{16}ClNO_2SNa$ (M+Na$^+$): 356.0482. Found: 356.0481.

(ii) Data for Compound 7b

Yield: 23%. $^1$H NMR (500 MHz, CDCl$_3$) δ 7.69 (d, 1H, J=8.5 Hz), 7.51 (dd, 1H, J=5.5, 0.5 Hz), 7.39 (dd, 1H, J=3.5, 0.5 Hz), 7.18-7.21 (m, 1H), 6.55-6.61 (m, 2H), 6.15 (s, 1H), 3.44 (q, 4H, J=7.0 Hz), 1.23 (t, 6H, J=7.0 Hz); $^{13}$C NMR (125 MHz, CDCl$_3$) δ 161.8, 156.8, 150.7, 148.2, 137.2, 128.6, 127.8, 127.7, 127.6, 108.6, 108.2, 107.1, 98.0, 44.8, 12.4; IR (neat, cm$^{-1}$) 3101, 2974, 1704, 1614, 1430, 1405, 1352, 1274, 1107; HRMS calculated for $C_{17}H_{17}NO_2SNa$ (M+Na$^+$): 322.0872. Found: 322.0871.

(iii) Data for Compound 7c

Yield: 42%. $^1$H NMR (500 MHz, CDCl$_3$) δ 7.73 (d, 1H, J=9.0 Hz), 7.20 (s, 1H), 7.09 (s, 1H), 6.60 (dd, 1H, J=9.0, 3.0 Hz), 6.57 (d, 1H, J=2.5 Hz), 6.13 (s, 1H), 3.44 (q, 4H, J=7.0 Hz), 2.35 (s, 3H), 1.23 (t, 6H, J=7.0 Hz); $^{13}$C NMR (125 MHz, CDCl$_3$) δ 161.9, 156.8, 150.7, 148.4, 138.5, 137.0, 130.9, 127.6, 123.3, 108.5, 107.9, 107.2, 98.0, 44.8, 15.8, 12.5; IR (neat, cm$^{-1}$) 2921, 1708, 1610, 1584, 1516, 1409, 1352, 1099; HRMS calculated for $C_{18}H_{19}NO_2SNa$ (M+Na$^+$): 336.1029. Found: 336.1029.

(iv) Data for Compound 7d

Yield: 22%. $^1$H NMR (500 MHz, CDCl$_3$) δ 7.75 (d, 1H, J=9.0 Hz), 7.21 (d, 1H, J=3.5 Hz), 6.85 (dd, 1H, J=2.5, 1.0 Hz), 6.58 (dd, 1H, J=9.0, 2.5 Hz) 6.56 (d, 1H, J=2.5 Hz), 6.11 (s, 1H), 3.43 (q, 4H, J=7.0 Hz), 2.57 (s, 3H), 1.22 (t, 6H, J=7.0 Hz); $^{13}$C NMR (125 MHz, CDCl$_3$) δ 162.0, 156.8, 150.6, 148.3, 143.0, 134.8, 128.9, 127.6, 126.2, 108.5, 107.5, 107.1, 98.0, 44.8, 15.4, 12.5; IR (neat, cm$^{-1}$) 2970, 1712, 1610, 1585, 1409, 1352, 1107; HRMS calculated for $C_{18}H_{19}NO_2SNa$ (M+Na$^+$): 336.1029. Found: 336.1026.

(h) General Procedure for Synthesis of Sensors 2a-d

POCl$_3$ (5.2 mL, 56.1 mmol) was added to DMF (10.8 mL, 139.5 mmol) at 0° C. in a flame-dried round bottom flask. The Vilsmeier reagent was stirred at ambient temperature for 45 min. The Vilsmeier reagent (5 mL) was added to a solution 7a-d in DMF (1 mL). The solution was stirred at ambient temperature for 12 hours. The resulting red solution was poured onto cold H$_2$O (100 mL), basified with saturated NaHCO$_3$ (50 mL), and extracted with CH$_2$Cl$_2$ (100 mL×3). The combined organic layers were dried over Na$_2$SO$_4$ and the solvent was removed in vacuo. The residue was purified by chromatography (90:10 hexanes:EtOAc→50:50 hexanes/EtOAc) to afford the desired formylated derivatives 2a-d as yellow oils.

(i) Data for Compound 2a

Yield: 78%. $^1$H NMR (500 MHz, CDCl$_3$) δ 10.00 (s, 1H), 7.30 (d, 1H, J=9.5 Hz), 7.02 (d, 1H, J=4.0 Hz), 6.89 (d, 1H, J=4.0 Hz), 6.57 (dd, 1H, J=9.0, 2.5 Hz), 6.49 (d, 1H, J=2.5 Hz), 3.47 (q, 4H, J=7.0 Hz), 1.24 (t, 6H, J=7.0 Hz); $^{13}$C NMR (125 MHz, CDCl$_3$) δ 187.7, 159.6, 157.5, 153.2, 152.4, 133.1, 131.1, 130.5, 128.8, 126.4, 113.2, 110.0, 109.1, 97.1, 45.2, 12.4; IR (neat, cm$^{-1}$) 2970, 1748, 1717, 1611, 1559, 1499, 1439, 1412; HRMS calculated for $C_{18}H_{16}ClNO_3SNa$ (M+Na$^+$): 384.0432. Found: 384.0432.

(ii) Data for Compound 2b

Yield: 54%. $^1$H NMR (500 MHz, CD$_2$Cl$_2$) δ 9.84 (s, 1H), 7.64 (dd, 1H, J=5.0, 1.0 Hz), 7.20-7.25 (m, 2H), 7.16 (dd, 1H, J=4.0, 1.0 Hz), 6.60 (dd, 1H, J=9.0, 2.5 Hz), 6.53 (d, 1H, J=2.5 Hz), 3.46 (q, 4H, J=7.5 Hz), 1.23 (t, 6H, J=7.5 Hz); $^{13}$C NMR (125 MHz, CD$_2$Cl$_2$) δ 188.0, 159.2, 157.9, 155.0, 153.5, 132.7, 130.9, 130.2, 128.7, 127.7, 114.0, 110.4, 109.8, 97.5, 45.7, 12.6; IR (neat, cm$^{-1}$) 2921, 1740, 1614, 1495, 1442, 1417, 1356; HRMS calculated for C$_{18}$H$_{17}$NO$_3$SNa (M+Na$^+$): 350.0821. Found: 350.0818.

(iii) Data for Compound 2c

Yield: 72%. $^1$H NMR (500 MHz, CDCl$_3$) δ 9.89 (s, 1H), 7.34 (d, 1H, J=8.5 Hz), 7.19 (s, 1H), 6.97 (s, 1H), 6.57 (dd, 1H, J=9.0, 2.5 Hz), 6.50 (d, 1H, J=2.5 Hz), 3.46 (q, 4H, J=7.0 Hz), 2.36 (s, 3H), 1.25 (t, 6H, J=7.0 Hz); $^{13}$C NMR (125 MHz, CDCl$_3$) δ 188.0, 158.8, 157.5, 155.3, 153.1, 138.1, 132.3, 131.8, 130.6, 124.0, 113.5, 109.7, 109.1, 97.1, 45.2, 15.6, 12.5; IR (neat, cm$^{-1}$) 2966, 1748, 1712, 1610, 1438, 1373, 1270, 1070, 731; HRMS calculated for C$_{19}$H$_{19}$NO$_3$SNa (M+Na$^+$): 364.0978. Found: 364.0977.

(iv) Data for Compound 2d

Yield: 83%. $^1$H NMR (500 MHz, CDCl$_3$) δ 9.92 (s, 1H), 7.41 (d, 1H, J=9.5 Hz), 6.99 (d, 1H, J=3.5 Hz), 6.88 (dd, 1H, J=3.5, 1.0 Hz), 6.58 (dd, 1H, J=9.0, 2.5 Hz), 6.52 (d, 1H, J=2.5 Hz), 3.48 (q, 4H, J=7.0 Hz), 2.61 (s, 3H), 1.26 (t, 6H, J=7.0 Hz); $^{13}$C NMR (125 MHz, CDCl$_3$) δ 188.1, 158.9, 157.5, 155.2, 153.0, 144.0, 130.7, 130.5, 129.5, 125.8, 113.5, 109.6, 109.1, 97.1, 45.2, 15.3, 12.5; IR (neat, cm$^{-1}$) 1744, 1610, 1561, 1499, 1422, 1266, 1123; HRMS calculated for C$_{19}$H$_{19}$NO$_3$SNa (M+Na$^+$): 364.0978. Found: 364.0975.

While the invention has been described in connection with specific embodiments thereof, it will be understood that the inventive method is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

What is claimed is:

1. A fluorescence sensing compound having the following formula:

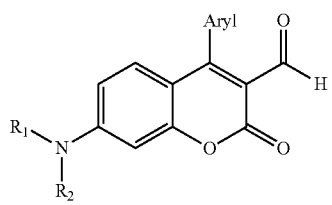

wherein
Aryl is an unsubstituted or substituted aryl moiety, wherein the aryl moiety is selected from the group consisting of a monocyclic or polycyclic benzene-based moiety and, if the benzene-based moiety is polycyclic, the benzene-based moiety is homocyclic or heterocyclic, wherein the benzene-based moiety has the following formula:

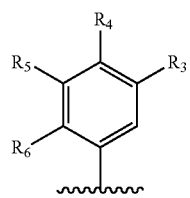

wherein R$_3$, R$_4$, R$_5$, and R$_6$ are each independently selected from the group consisting of hydrogen, alkyl, alkylene, aryl, cycloalkyl, halo, hydroxyl, alkoxyl, aryloxy, alkylthio, arylthio, carboxyl, and alkoxycarbonyl, or one or more of R$_3$, R$_4$, R$_5$, and R$_6$, which are adjacent, are each a constituent of a fused unsubstituted or substituted aryl; and
R$_1$ and R$_2$ are each independently selected from the group consisting of hydrogen, alkyl, alkylene, aryl, and cycloalkyl.

2. The fluorescence sensing compound of claim 1, wherein the benzene-based moiety has a formula selected from the group consisting of the following:

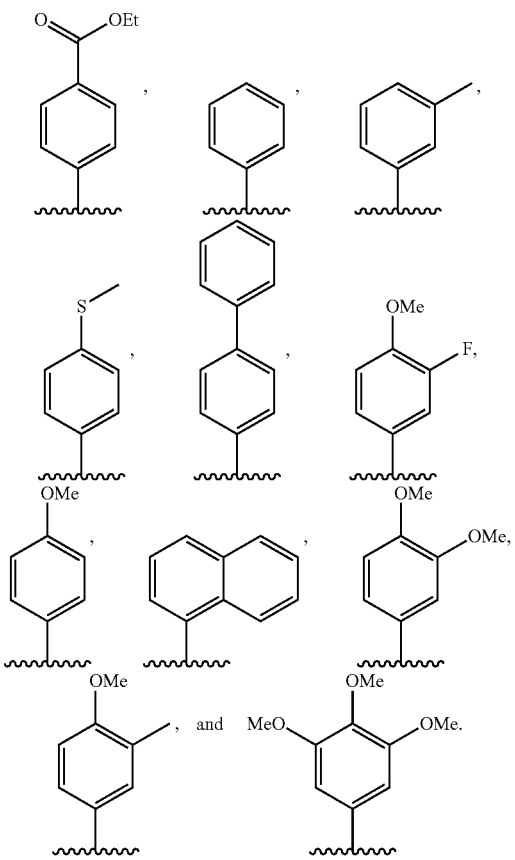

3. The fluorescence sensing compound of claim 1, wherein the benzene-based moiety is a naphthalene-based moiety having the following formula:

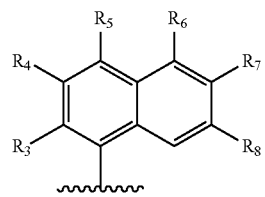

wherein R$_3$, R$_4$, R$_5$, R$_6$, R$_7$, and R$_8$ are each independently selected from the group consisting of hydrogen, alkyl, alkylene, aryl, cycloalkyl, halo, hydroxyl, alkoxyl, aryloxy, alkylthio, arylthio, carboxyl, and alkoxycarbonyl, or one or more of R$_3$, R$_4$, R$_5$, R$_6$, R$_7$, and R$_8$, which are adjacent, are each a constituent of a fused unsubstituted or substituted aryl.

4. A method of detecting primary amine containing analyte in a biological sample, comprising:

a. contacting the biological sample with a fluorescent sensor compound having the following formula:

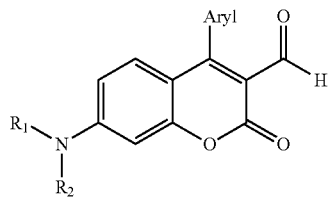

wherein Aryl is an unsubstituted or substituted aryl moiety, and $R_1$ and $R_2$ are each independently selected from the group consisting of hydrogen, alkyl, alkylene, aryl, and cycloalkyl; and b. detecting the presence or absence of fluorescence in the sample, wherein the presence of fluorescence indicates the presence of primary amine in the sample.

5. The method of claim 4, wherein the aryl moiety is selected from the group consisting of (i)monocyclic or polycyclic benzene-based moiety, and, if the benzene-based moiety is polycyclic, the benzene-based moiety is homocyclic or heterocyclic, and (ii) monocyclic or polycyclic heterocyclopentadiene-based moiety having one or more heteroatoms selected from the group consisting of oxygen, sulfur, and nitrogen.

6. The method of claim 5, wherein the aryl moiety is the benzene-based moiety, wherein the benzene-based moiety has the following formula:

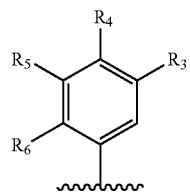

wherein $R_3$, $R_4$, $R_5$, and $R_6$ are each independently selected from the group consisting of hydrogen, alkyl, alkylene, aryl, cycloalkyl, halo, hydroxyl, alkoxyl, aryloxy, alkylthio, arylthio, carboxyl, alkoxycarbonyl, or one or more of $R_3$, $R_4$, $R_5$, and $R_6$, which are adjacent, are each a constituent of a fused unsubstituted or substituted aryl.

7. The method of claim 6, wherein the benzene-based moiety has a formula selected from the group consisting of the following:

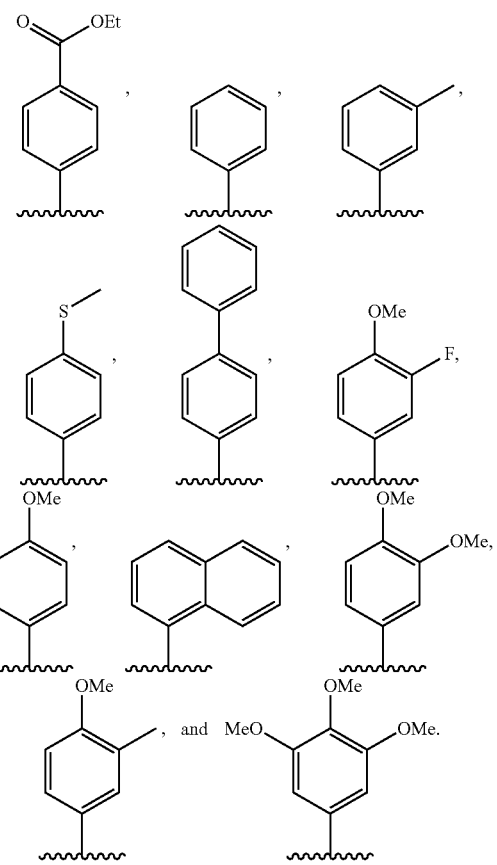

8. The method of claim 6, wherein the benzene-based moiety is a naphthalene-based moiety having the following formula:

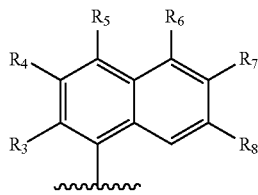

wherein $R_3$, $R_4$, $R_5$, $R_6$, $R_7$, and $R_8$ are each independently selected from the group consisting of hydrogen, alkyl, alkylene, aryl, cycloalkyl, halo, hydroxyl, alkoxyl, aryloxy, alkylthio, arylthio, carboxyl, and alkoxycarbonyl, or one or more of $R_3$, $R_4$, $R_5$, $R_6$, $R_7$, and $R_8$, which are adjacent, are each a constituent of a fused unsubstituted or substituted aryl.

* * * * *